(12) United States Patent
Suhami

(10) Patent No.: US 6,795,199 B2
(45) Date of Patent: Sep. 21, 2004

(54) METHOD AND APPARATUS FOR DISPERSION COMPENSATED REFLECTED TIME-OF-FLIGHT TOMOGRAPHY

(76) Inventor: Avraham Suhami, 1496 Almaden Rd., Apt. 307, San Jose, CA (US) 95125

( * ) Notice: Subject to any disclaimer, the term of this patent is extended or adjusted under 35 U.S.C. 154(b) by 103 days.

(21) Appl. No.: 10/199,288

(22) Filed: Jul. 18, 2002

(65) Prior Publication Data

US 2003/0025917 A1 Feb. 6, 2003

Related U.S. Application Data

(60) Provisional application No. 60/305,953, filed on Jul. 18, 2001.

(51) Int. Cl.$^7$ .............................................. G01B 11/30
(52) U.S. Cl. ...................................... 356/601; 356/607
(58) Field of Search ................................. 356/601, 606, 356/607, 608, 364, 369; 250/559.05, 559.06, 559.09, 559.22; 382/154; 351/206, 215, 221

(56) References Cited

U.S. PATENT DOCUMENTS

6,011,626 A * 1/2000 Hielscher et al. ........... 356/367

* cited by examiner

Primary Examiner—Frank G. Font
Assistant Examiner—Roy M. Punnoose

(57) ABSTRACT

The invention discloses a time-of-flight method and apparatus for rapid and high resolution measurement of the optical characteristics of a set of superimposed thin layers within an object, penetrated by an illuminating beam of light. The very high temporal, spectral and spatial resolutions are obtained by illuminating the object with a femtosecond laser and collecting the data characteristic of the different layers simultaneously, by sampling the scattered radiation in the time domain, using a chain of linked non-linear gates.

21 Claims, 20 Drawing Sheets

Fig. 19
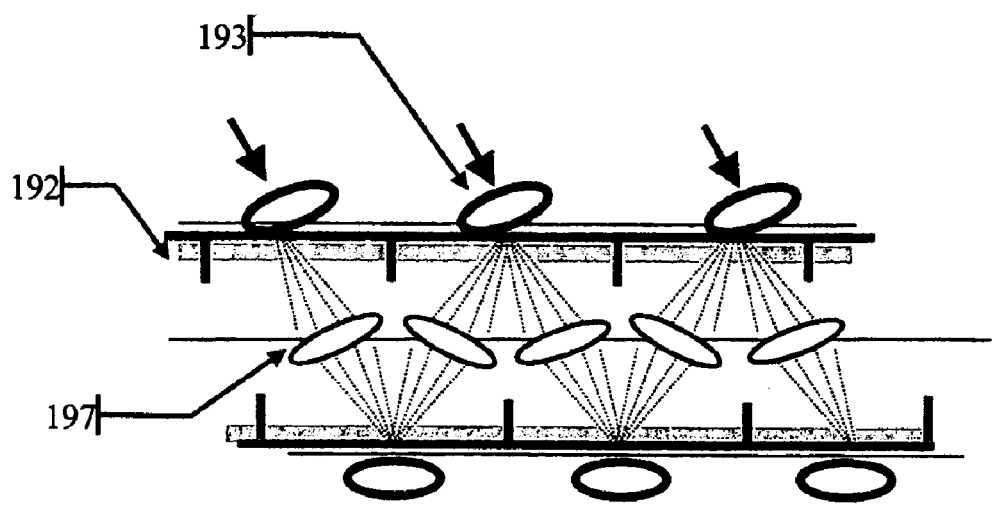
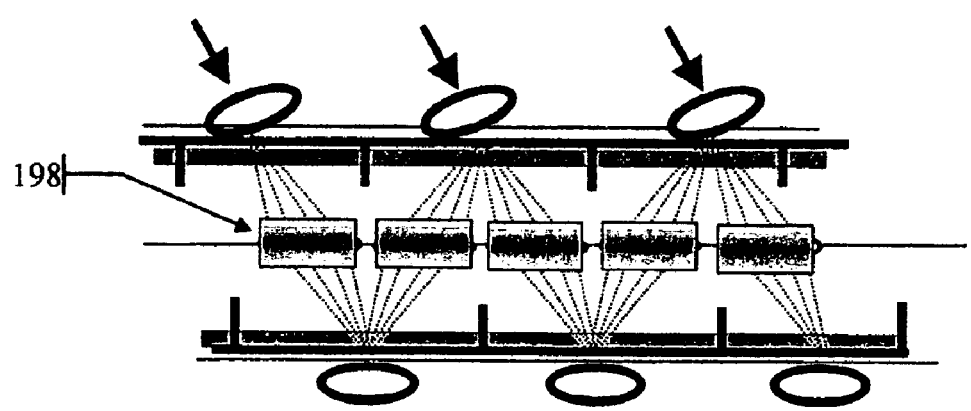

METHOD AND APPARATUS FOR DISPERSION COMPENSATED REFLECTED TIME-OF-FLIGHT TOMOGRAPHY

This application claims the benefit of the filing of U.S. Provisional Patent Application Serial No. 60/305,953 filed on Jul. 18, 2001 which included provisional application No. 60/280,331 filed on Apr. 2, 2001 in its entirety.

FIELD OF THE INVENTION

This invention relates to optical imaging

Relevant Patents

U.S. Pat. No. 5,076,672 All-optical switch apparatus using a nonlinear etalon Tsuda, et al.
U.S. Pat. No. 5,275,168 Time-gated imaging through dense-scattering materials using stimulated Raman amplification, Reintjes, J et al.
U.S. Pat. No. 5,291,267 Optical low-coherence reflectometry using optical amplification Sorin et al
U.S. Pat. No. 5,299,170 Apparatus for measuring pulse width with two photon absorption medium,. Shibata et al
U.S. Pat. No. 5,321,501 Method and apparatus for optical imaging with means for controlling the longitudinal range of the sample, Swanson E. et al.
U.S. Pat. No. 5,418,797 Time gated imaging through scattering material using polarization and stimulated Raman amplification, Bashkansky et al
U.S. Pat. No. 5,489,984 Differential ranging measurement system and method utilizing ultrashort pulses Hariharan, et al.
U.S. Pat. No. 5,491,524 Optical coherence tomography corneal mapping apparatus Hellmuth, T et al
U.S. Pat. No. 5,549,114 Short coherence length, doppler velocimetry system Petersen, C et al.
U.S. Pat. No. 5,530,544 Method and apparatus for measuring the intensity and phase of one or more ultrashort light pulses and for measuring optical properties of materials Trebino, R et al.
U.S. Pat. No. 5,570,182 Method for detection of dental caries and periodontal disease using optical imaging, Nathel; H et al.
U.S. Pat. No. 5,585,913 Ultrashort pulsewidth laser ranging system employing a time gate producing an autocorrelation and method therefore Hariharan, A et al.
U.S. Pat. No. 5,648,866 Optimized achromatic phase-matching system and method Trebino et al.
U.S. Pat. No. 5,862,287 Apparatus and method for delivery of dispersion compensated ultrashort optical pulses with high peak power Stock et al.
U.S. Pat. No. 5,936,732 Apparatus and method for characterizing ultrafast polarization varying optical pulses Smirl et al.
U.S. Pat. No. 5,920,373 Method and apparatus for determining optical characteristics of a cornea Bille, J
U.S. Pat. No. 5,920,390 Fiberoptic interferometer and associated method for analyzing tissue Farahi, et al.
U.S. Pat. No. 5,975,697 Optical mapping apparatus with adjustable depth resolution Podoleanu, A et al.
U.S. Pat. No. 5,994,690 Image enhancement in optical coherence tomography using deconvolution Kulkarni, M et al.
U.S. Pat. No. 6,002,480 Depth-resolved spectroscopic optical coherence tomography Izatt; J. et al
U.S. Pat. No. 6,006,128 Doppler flow imaging using optical coherence tomography Izatt; J. et al
U.S. Pat. No. 6,008,899 Apparatus and method for optical pulse measurement Trebino; R et al.
U.S. Pat. No. 6,023,057 Device for determining the phase errors of electromagnetic waves Gaffard et al.
U.S. Pat. No. 6,053,613 Optical coherence tomography with new interferometer Wei Jay et al.
U.S. Pat. No. 6,095,651 Method and apparatus for improving vision and the resolution of retinal images Williams, D et al
U.S. Pat. No. 6,111,645 Grating based phase control optical delay line Tearney, et al.
U.S. Pat. No. 6,134,003 Method and apparatus for performing optical measurements using a fiber optic imaging guidewire, catheter or endoscope Tearney et al.
U.S. Pat. No. 6,199,986 Rapid, automatic measurement of the eye's wave aberration Williams, D et al
U.S. Pat. No. 6,191,862 Methods and apparatus for high speed longitudinal scanning in imaging systems Swanson; A. et al.
U.S. Pat. No. 6,195,617 B I Autocorrelation of ultrashort electromagnetic pulses Reid et al.
U.S. Pat. No. 6,201,608 Method and apparatus for measuring optical reflectivity and imaging through a scattering medium Mandella et al.,
U.S. Pat. No. 6,226,112 Optical Time-division-multiplex system by Denk, et al.
U.S. Pat. No. 6,249,630 Apparatus and method for delivery of dispersion-compensated ultrashort optical pulses with high peak power Stock et al
U.S. Pat. No. 6,256,102 Dual-beam low-coherence interferometer with improved signal-to-noise ratio Dogariu A et al.
U.S. Pat. No. 6,291,824 Apparatus and method for high-bandwidth optical tomography Battarbee, et al
U.S. Pat. No. 6,356,693 semiconductor optical pulse compression waveguide, Shimazu et al.

Other Publications

"Imaging Objects Hidden in a Highly Scattering Media Using Femtosecond Second-Harmonic-Generation Cross-Correlation Time Gating", Yoo et al, Optics Letters, July 1991, pp. 1019–1021. Jenkins & White, fundamental of Optics, McGraw-Hill, 1957

BACKGROUND OF THE INVENTION

It is well known that a Michelson Interferometer enables to make precise distance and incremental displacement measurements by observing the fringes formed by the interference of coherent light waves. The interference between light waves that have traveled along different pathways is limited by the coherence length of the light source. As long as the different pathways differ by less than the coherence length of the source, interference will result in formation of fringes.

Optical Coherent Tomography (OCT) makes use of a Michelson interferometer to image the topography of the layers behind the surface of a tissue by scanning "same-depth" layers. This is achieved by precise balancing of the legs of the interferometer, so that the depth information is obtained by observing the interference fringes when the two legs of the interferometer are within the coherent length of the illuminating light source. Changing the length of one of the paths enables to focus on a layer at a depth that differs by the length changed. However as fringes of equal intensity are obtained with widely differing path lengths, for as long as the interfering light waves are coherent, light sources with short coherence lengths such as superluminescent diodes are used, so as to minimize this ambiguity. This setup greatly facilitates the calibration of the interferometer as no interference fringes are obtained when the path lengths between the two legs of the interferometer differ by more than the coherence length.

However, it is important to realize that the fringes observed with any light source, originate from the interference of light coming from many oscillators which emit light randomly and non-coherently one from the other. Low coherence length sources are limited in resolution by the randomness of the coherence lengths of the different oscillators and the FWHM of the group of fringes is what determines the "path-length difference" resolution and not the FWHM of a single fringe. It is also important to realize that the non-coherence among the various oscillators, also manifests itself in a high uniform background over which the fringe pattern is observed, thus the SNR obtained with low coherence length superluminescent diodes is much worse than the SNR of a fringe pattern obtained with highly coherent sources.

The conventional Optical Coherent Tomography (OCT) technique, (see for example U.S. Pat. No. 5,321,501, Method and apparatus for optical imaging with means for controlling the longitudinal range of the sample, Swanson E. et al.) uses a low coherence light source, to minimize the spread of the fringe pattern and thus increase the "path-length difference" precision.

OCT is constrained by the need to sequentially adjust the depth of the imaged layer by incrementally changing one of the legs of the Michelson interferometer, either mechanically with a retroreflector, by stretching the optical fiber with a piezoelectric motor or by a combination of an acousto-optic deflector, a grating and a mirror (see U.S. Pat. No. 6,111,645 Grating based phase control optical delay line Tearney, et al.). In spite of all the heroic efforts, it takes ~100 microseconds to change the delay, position and balance the interferometer onto a new layer.

OCT is also limited by "speckles", a background generated by the interference with the coherent multiple back-scattered light, that originates from a spherical volume with a radius equal to the low coherent length of the source.

Ultrafast femtosecond lasers have several important advantages over CW or long-pulse lasers. They permit to achieve high peak power while the average power is relatively low and thus can stimulate nonlinear processes such as second harmonic generation, and amplification. through Stimulated Raman Scattering.

Time gating of Raman amplified signals transmitted through a light diffusing medium in order to locate a strongly absorbing region within such medium, has been demonstrated by Reintjes, et al (see U.S. Pat. No. 5,275,168 Time-gated imaging through dense-scattering materials using stimulated Raman amplification.). Properly adjusting the time delays enable to amplify only the early arriving non-scattered photons, while leaving the multiple scattered diffuse light non-amplified.

U.S. Pat. No. 5,418,797 Time gated imaging through scattering material using polarization and stimulated raman amplification by Bashkansky et al, teaches how to reject the diffuse light by making use of the different polarizations of the diffuse and the non-scattered beams. Note that transmission and reflection geometries are totally different. In a reflection geometry, there are no non-scattered photons, and photons scattered backwards from the different layers, exhibit a continuous distribution in their time-of-flight.

Non-linear crystal such as KDP, KTP or BBO are used in commercially available autocorrelators to establish optical coincidence between two coherent branches of short pulses fed co-linearly into them. The two coherent waves generate a Second Harmonic Generation (SHG) wavelength at half the wavelength, during the spatially overlapping time period and may be detected by a photodetector. The pulse shape is determined by delaying one of the two coherent waves and measuring the intensity at the output of the non-linear crystal. Alternatively measuring the intensities of the spectral content of the pulse as a function of delay will give both its intensity shape and phase.

A narrow temporal width is associated with a wide spectral distribution and thus a single femtosecond laser may be used for multiwavelength excitation of the sample.

U.S. Pat. No. 5,585,913 Ultrashort pulsewidth laser ranging system employing a time gate producing an autocorrelation and method therefore by Hariharan, A et al. teaches a method to measure the topography of a surface by correlating the illuminating femtosecond pulse and the radiation reflected from the examined surface using an SHG (Second Harmonic Generation) crystal.

U.S. Pat. No. 6,249,630 "Apparatus and method for delivery of dispersion-compensated ultrashort optical pulses with high peak power" by Stock et al. teaches to stretch the width of optical pulses in order to reduce the peak power transmitted through a fiber and then recompressing it before delivering it to the target.

It is well known that scattering changes the polarization of the scattered wave and therefore using proper polarization analyzers, single scattered photons may be separated from multiple scattered ones.

The speed of light decreases in direct proportion to the increase of the refraction index of the medium in which it propagates. Thus a wide beam passing through a medium whose refraction index changes across the width of the beam will have its different components moving ahead or lagging behind. Thus GRadient INdexed materials that have gradually changing refraction indexes may be used to temporally reshape the wavefront and compensate for time dispersion.

BRIEF SUMMARY OF THE INVENTION

The invention is an imaging device consisting in a high resolution time-of-flight measurement, of a temporally narrow, but spectrally wide, light beam generated by a femtosecond laser source, after being back-scattered by a relatively thick object, whose layers are to be characterized. Those characteristics include, absorbing, elastic and inelastic scattering cross sections, including intensity, polarization, spectral content and the angular distribution of the beam scattered from the various layers penetrated by the illuminating beam. The impinging beam invariably penetrates a certain depth of the object and sometimes traverses or is scattered by it, the degree of which depends on the beam's wavelength, intensity, angle of incidence and the composition of the scattering medium, that collectively determine the degree of scattering and absorption cross sections.

Contrary to prior art methods that measure one distance at a time, it is a purpose of this invention to collect the data pertaining to the characteristics listed above from all the voxels along the axis of penetration, during a single femtosecond pulse of the illuminating laser, process and store such data during the period between two consecutive pulses of the high repetition rate femtosecond laser.

The time of flight of the back scattered photons and consequently their depth coordinate is determined by measuring their coincidence with the illuminating ultrashort pulse. Such coincidence is established by a time-gate that may be a non-linear medium such as an SHG (Second Harmonic Generation) medium, a Raman-active medium, a non-linear fiber coupler, or a phase-sensitive interferometer. Obviously the speed of the time-gate determines the time-of-flight accuracy and the ability to temporally differentiate between photons back-scattered from consecutive layers, thus determining the degree of characterization of the different layers.

The temporally narrow illuminating beam, when temporally stretched and wavelength filtered will cause its transmitted spectral components to arrive at the scattering body sequentially and then back-scattered. In this case the temporal separation of the spectral components each from the other, has to be larger than the temporal spread of the illuminating pulse caused by back-scattering from the different layers, but smaller than the repetition rate of the femtosecond laser. For example a 10 fs pulsewidth of a f=100 MHz femtosecond laser, which illuminates the target every $(1/f)=10$ nsec., will be temporally spread to $\Delta T_L = 5$ psec after being back scattered from a L=1 mm thick tissue; thus the temporal separation between consecutive wavelengths has to be larger than $\Delta T_L = 5$ psec, say $\Delta t_\lambda = 10$ psec. In this case, the total number of wavelengths that can be inserted between two consecutive pulses of the femtolaser is $1/f\Delta t_\lambda = 10^3$. When the back-scattering is elastic, the wavelength of the back-scattered photons will not change and in addition to their time of flight sorting, they may be classified in real time according to the wavelength of the illuminating beam by passing them through a passive component such as a grating.

The wavelength of the illuminating beam may also be changed by physically inserting an appropriate interference filter on the path of the temporally stretched femtosecond pulse, using a fast translating motor.

Measuring the spectral back-scattering intensity of a body, while rapidly scanning it, enables to dynamically map regions and structures exhibiting different absorption cross sections. Thus for example the web of vessels transporting the blood may be mapped and the state of oxygenation of the surrounding cells, as a function of the systolic or diastolic pressure may be recorded.

Spectral and temporal cross-correlation between the impinging and scattered beams enables to extract the change of phase, enabling to map same-phase biological tissue structures as indicative of their equivalence.

The extremely narrow pulses having high instantaneous power, result in a high signal/noise ratio and enable to collect all the needed information for a single spot, during a single femtosecond pulse, obviating the need to integrate the signal for a relatively long time, a process usually necessary in order to improve the Signal-to-Noise ration (SNR).

The simultaneous collection of all the time-of-flight data of the photons back-scattered from the different layers, is made possible by a chain of linked AND time-gates equivalent to an "optical serial-to-parallel converter" that converts the inherently serial "time-of-flight" information, to parallel optical signals, on the fly, each signal representing the intensity of the back-scattered photons for a different time-of-flight. This method reduces the total volumetric imaging time by a factor equal to the number of layers to be imaged, in fact opening up applications that are not practical to do with the prior-art methods, such as OCT , Confocal microscopy or time-of-flight ranging.

It has to be realized that collecting the back-scattered photons from one layer at a time, as is done by prior-art methods, not only takes more time but is also wasteful from the point of view of photon statistics and signal-to-noise ratio (SNR), given the minimal time of illumination required in all dynamic applications where the object is moving. The impinging beam always penetrates the maximal allowable depth determined by the physics of the interaction, and is scattered by all the interim layers. Limiting the collection of back-scattered photons to the surface or one layer, and rejecting the photons back-scattered from all the other layers, is a tremendous waste, a waste that increases with improvement of the axial resolution.

To illustrate our argument numerically, if 100 layers are imaged sequentially, one at a time, 99% of the information is lost and given a fixed total time of imaging, the SNR will be $(100)^{1/2}=10$ times worse. In Ophthalmology for example, where damage to the retina has to be avoided and therefore the illuminating intensity limited, throwing away 99% of the information leads to unsatisfactory diagnostic images.

In addition to their precisely determined time-of-arrival, scattered photons may also be sorted according to their state of polarization, thus separating, the once back-scattered photons, from double and multiple scattered photons. The extremely narrow illumination in time of one single voxel combined with a narrow time-gate, reduces drastically the multiple scattering. For example if only 1% of the beam is scattered from within the time defined voxel, twice-scattered photons within the same time-voxel constitute $(1\%) \times (1\%) = 10^{-4}$ of the impinging beam or 1% of the single scattered photons. The solid angle to the collecting detector further reduces the portion of double or multiple scattered (more than twice) scattered photons.

The extremely short information collection time per pixel, combined with a high repetition rate source and high speed beam deflectors further enhanced by the ability to collect the information from all the layers simultaneously, result in data collection and characterization of large volumes, in exceptionally short times.

Thus for example data characterizing 1 million voxels (100×100×100 pixels), can be collected within 100 microseconds. Such data collection speed, with spatial resolutions of the order of cellular dimensions, enables to follow kinetics of well defined biological structures. The capabilities described above when applied to vascular and arterial high resolution imaging of blood vessels, by applying dual wavelength illumination, enables to follow temporally, the oxygenation kinetics at the cellular level. Such processes may discriminate cancerous growths from normal tissue based on observation of angiogenesis coupled with the existence of hypoxic regions and polarization characteristics as a function of blood flow. The capability to follow blood kinetics at the millisecond time scale combined with cellular spatial resolutions, enables to follow neurological functions. Dynamic imaging of the vasculature and microvessels enable to discern developing aneurysms and follow embolisms, immediately below the surface.

The time-of-flight method may be used to determine the eyeball's optical aberrations by measuring directly the shape of the light wave emanating from a point on the retina, when this point is illuminated with a narrow light beam. The arrival time of the reflected/back-scattered rays are measured sequentially for a large matrix, within a short time and the phase of each of the rays is calculated by measuring the cross-correlation with the illuminating beam.

BRIEF DESCRIPTION OF THE DRAWINGS

FIG. 19 shows the correction of the spatial dispersion experienced by the analog signal when reflected from one plate to another

DETAILED DESCRIPTION OF PREFERRED EMBODIMENTS

Figure 1:
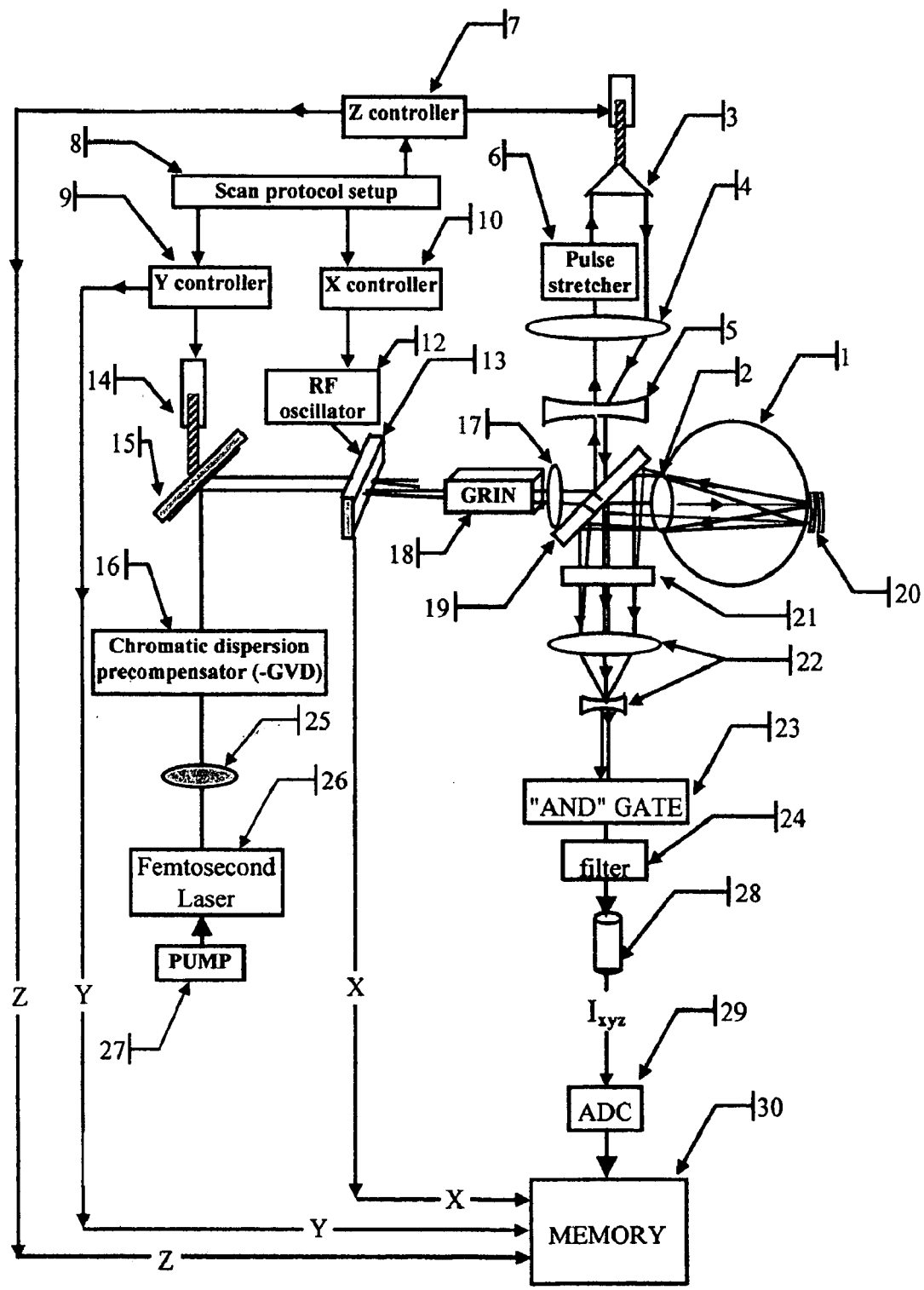
FIG. 1 shows a system for measuring the topography of a surface using the time of-flight method.

FIG. 1 illustrates the "reflected time-of-flight tomography" method as implemented in the measurement of the density of a single layer within the retina of the eye. It is understood that the retina is chosen to exemplify the method which is not limited to the retina and is applicable to any thin surface penetrated by the illuminating beam, biological or non-biological, consisting of a multitude of layers. A Femtosecond laser 26 pumped by a pump 27, emits light pulses as short as several femtoseconds ($10^{15}$ sec) and when has a spectral bandwidth determined by the inequality $(\Delta v)(\Delta \tau) \geq 1$. Preferably, for the retinal shape and thickness measurement application to be described in the following, femtolasers with a central frequency of 690–1060 nm are suitable, as this range of wavelengths constitute a good compromise between the low absorption in water and retinal tissue and higher absorption of blood.

| Absorption in $cm^{-1}$ | 690 nm | 808 nm | 1.06 $\mu$ |
|---|---|---|---|
| Oxyhemoglobin in water | 1.5 | 4.3 | 4 |
| Deoxyhemoglobin in water | 11.0 | 4.3 | 0.40 |
| Carboxyhemoglobin | 0.3 | 0.05 | ~0 |
| Water | 0.005 | 0.020 | 0.12 |

Figure 4:
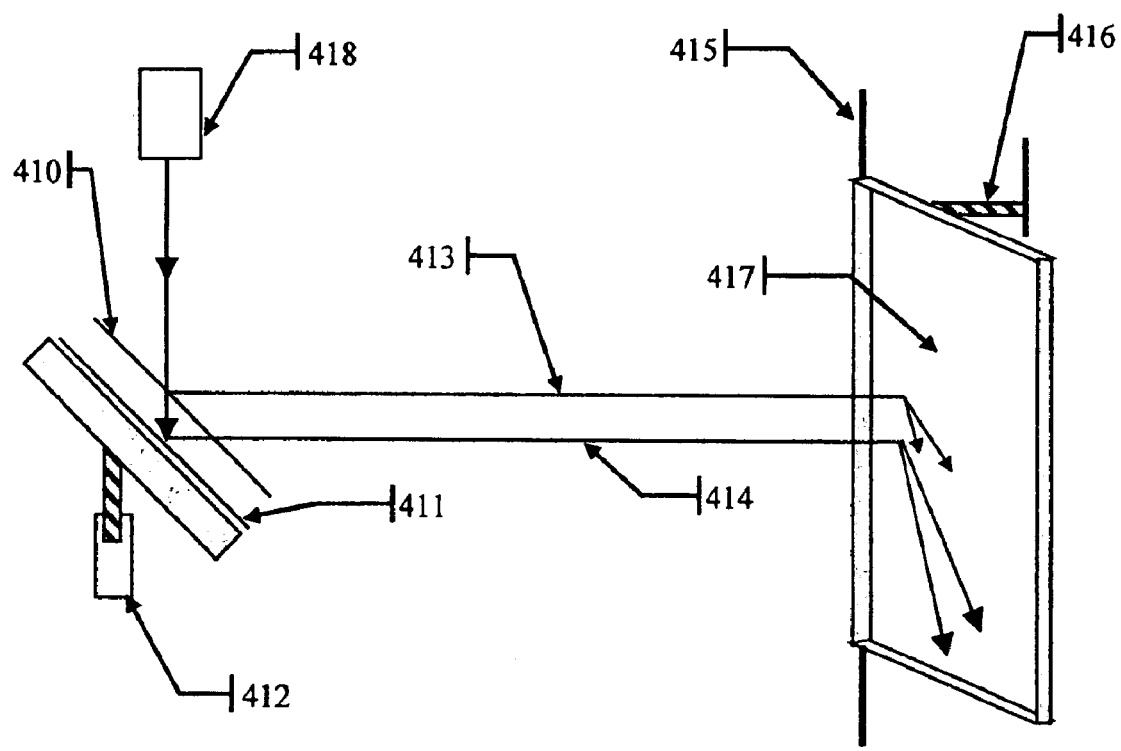
FIG. 4 shows a mechanical linear beam translator

The narrow beam of light that emerges from the femtolaser passes through several optical components 25, 13, 15, 17, 18, 19 and travels in free space until it reaches the patient's eye's lens, traverses the vitreous humor, until it strikes the retina. As the different spectral components of the femtosecond beam travel at different speeds the temporally narrow beam experiences Group Velocity Dispersion (GVD) and widens. Therefore in order to get back the original narrow width at the time that the beam hits the retina the expected spectral dispersion may be compensated for, by giving the original beam a negative Group Velocity Dispersion (NGVD) 16. The technique of changing the Group Velocity Dispersion by using two or more Prisms or Gratings properly positioned so as to direct the different wavelengths onto paths of different lengths, is well known in the art. The collimated 25, spatially narrow beam is reflected by a mirror 15 that may be translated by a piezo-electric motor 14, so that the reflected beam is moved along the Y axis onto parallel paths. FIG. 4 depicts the parallel paths 413 and 414 resulting from the movement of mirror 411 to a position 410 along the Y axis. The scan along the X axis may be performed by one of several devices. In FIG. 1 an acousto-optical deflector 13 based on a $TeO_2$ crystal operating at very high frequency of ~1 GHz supplied by a tunable RF oscillator 12, is depicted. Changing the RF frequency changes the "step" of the grating formed by the standing ultrasound wave and thus causes any transmitted beam to be deflected to a different angle; with acousto-optic deflectors 1°–2° deflections may be achieved within 10 $\mu$sec.

Figure 5A:
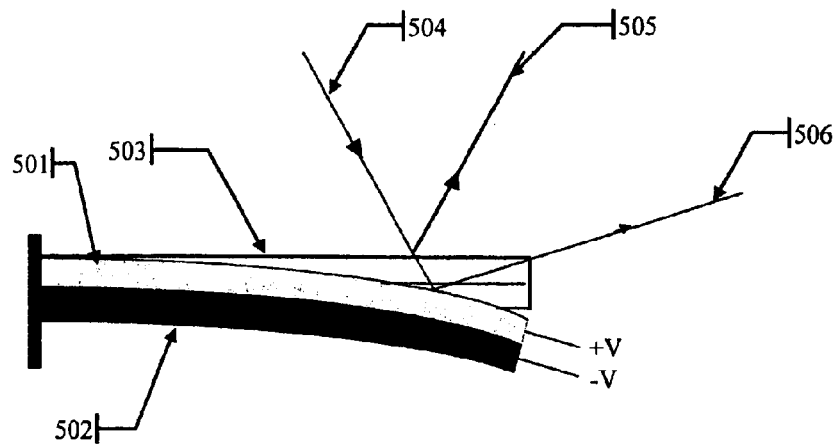
FIG. 5A illustrates the operation of a piezo-electric beam deflector
Figure 5B:
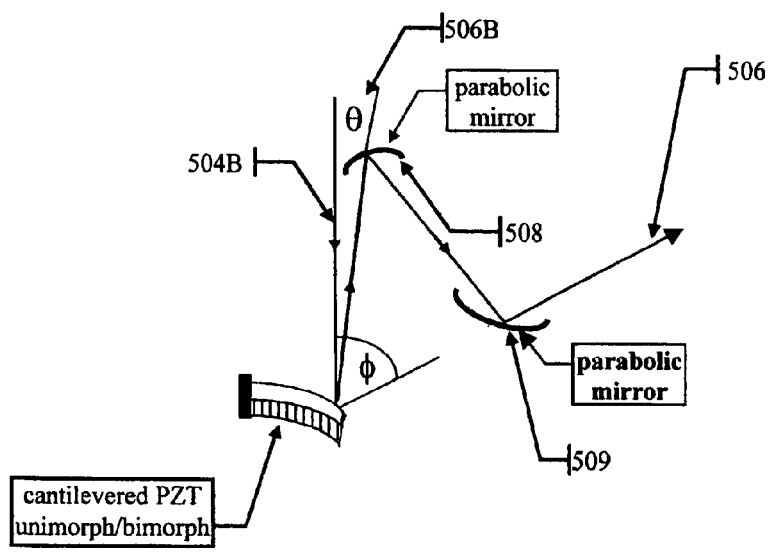
FIG. 5B illustrates the amplification of a small deflection caused by a piezoelectric bimorph or unimorph beam deflector

FIG. 5A depicts another fast beam deflector made from two piezoelectric plates glued back-to-back or on a common substrate, a cantilevered bimorph. While a positive voltage along its length is applied to plate 501 causing elongation, a negative voltage is applied to plate 502 causing it to shorten. The combined result is a bending of the plates to accommodate the deformation. An incoming beam of light 504 initially reflected to 505 will after the deformation be deflected to 506. Changing the applied voltages at a high frequency will make the combined plate vibrate and deflect the incoming beam, forth and back. Very high stable vibration frequencies of the order of several MHz may be obtained when the induced frequency equals the mechanical resonant frequency of the cantilevered Piezo-electric bimorph or unimorph. The small angular aperture of the reflected beam due to the small amplitude of the vibrating tip may be amplified by properly positioned mirrors 508 and 509 that also serve to focus the deflected beam as shown in FIG. 5B. Another mechanical solution for a fast scanner is to use miniature motors having very high revolution speeds of up to 60,000 rpm or one revolution per msec equivalent to 3.6° per 10 μsec. A 100 faceted mirrored polygon rotated by the miniature motor will deflect incoming beams by 3.6° every 10 μsec.

Figure 3:
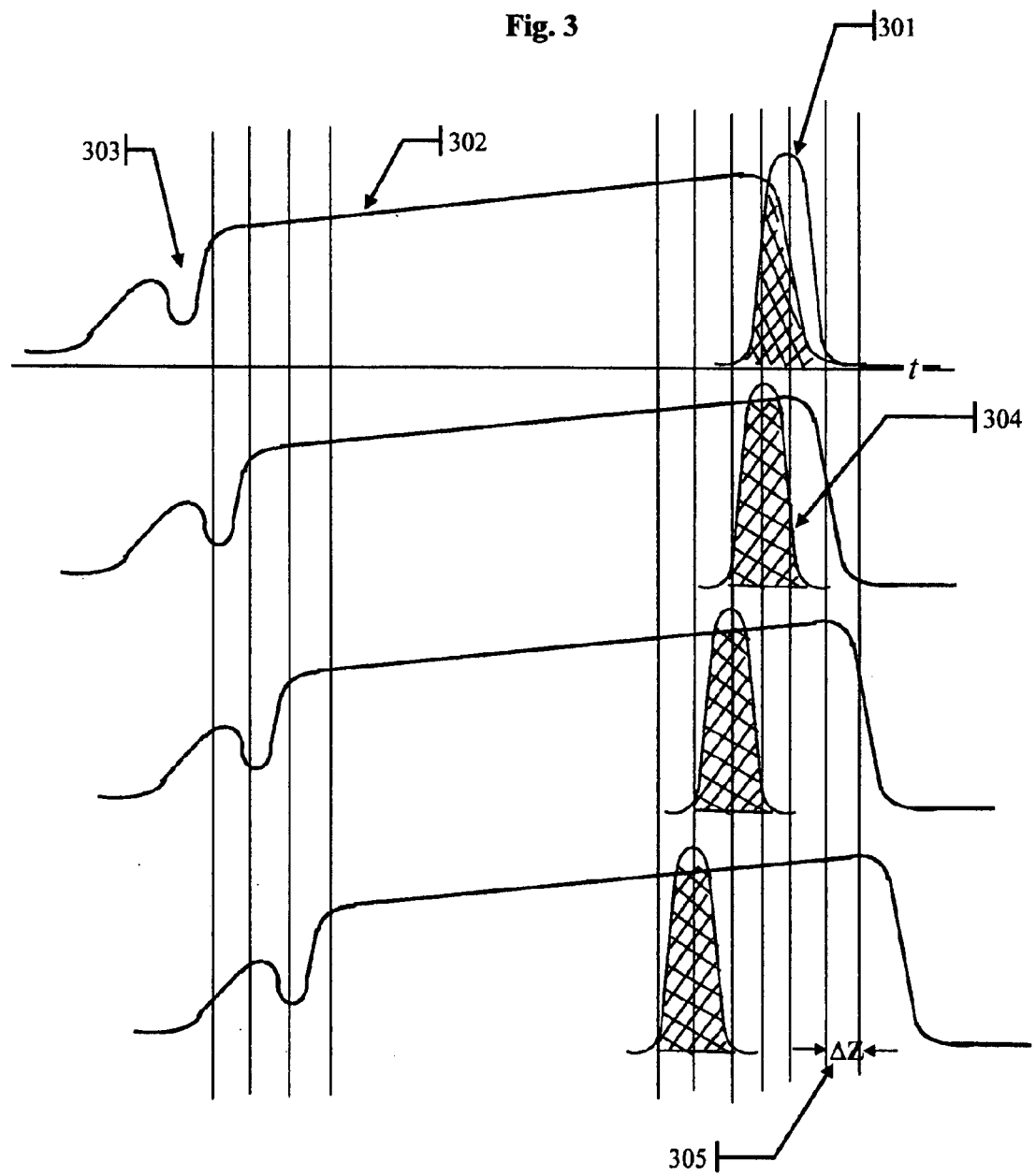
FIG. 3 shows the intensities of the ultrashort illuminating light pulse superimposed on the backscattered light continuum, as a function of time

Returning to FIG. 1 an X deflector with an aperture of ±1° scanning from a distance of approximately 12" may scan a 1 cm line within 10 μsec. The beam then passes through a longitudinal GRIN (GRadient INdex) bar 18 that has a decreasing refraction index from its axis and outward. The dimensions of the GRIN bar is determined by the maximal deflection angle of the X deflector, so as to compensate in time for the longer path. Optics 17 serve to focus the narrow beam transversally. The beam then goes through a beam splitter 19 that transmits part of the beam into the eye and reflects the other part to a retroreflector 3 that changes the path length. The beam is split in unequal proportions as the aim is to maximize the signal-to-noise ratio (SNR) of the intensity of the coincident output exiting the AND time-gate which is proportional to the multiplication of the gating signal and the back-scattered signal over the noise which is dependent on the geometry of the measurement and scattering characteristics. Thus the optimal proportions are best found experimentally. The narrow pulse passes through a pulse stretcher 6 that widens the pulse by introducing spectral dispersion in a controlled way by changing the distances between the Prisms or Gratings. The temporal width of the newly stretched pulse is what determines the thickness of the layer in the Z direction (depth) that is imaged. The beam returning from the retroreflector passes through lenses 4 and 5 that center the beam along the optical axis. The beam that hits the back of the eye is attenuated/back scattered by the different layers of the retina and is finally absorbed in the choroid. As depicted in FIG. 3 the back scattered photons from the different layers constitute a continuum 302 on a time scale; as the beam is attenuated as it penetrates the retina and the solid angle formed by the scattering center and the pupil keeps decreasing as a function of depth, the intensity declines as illustrated in 302.

Figure 20:
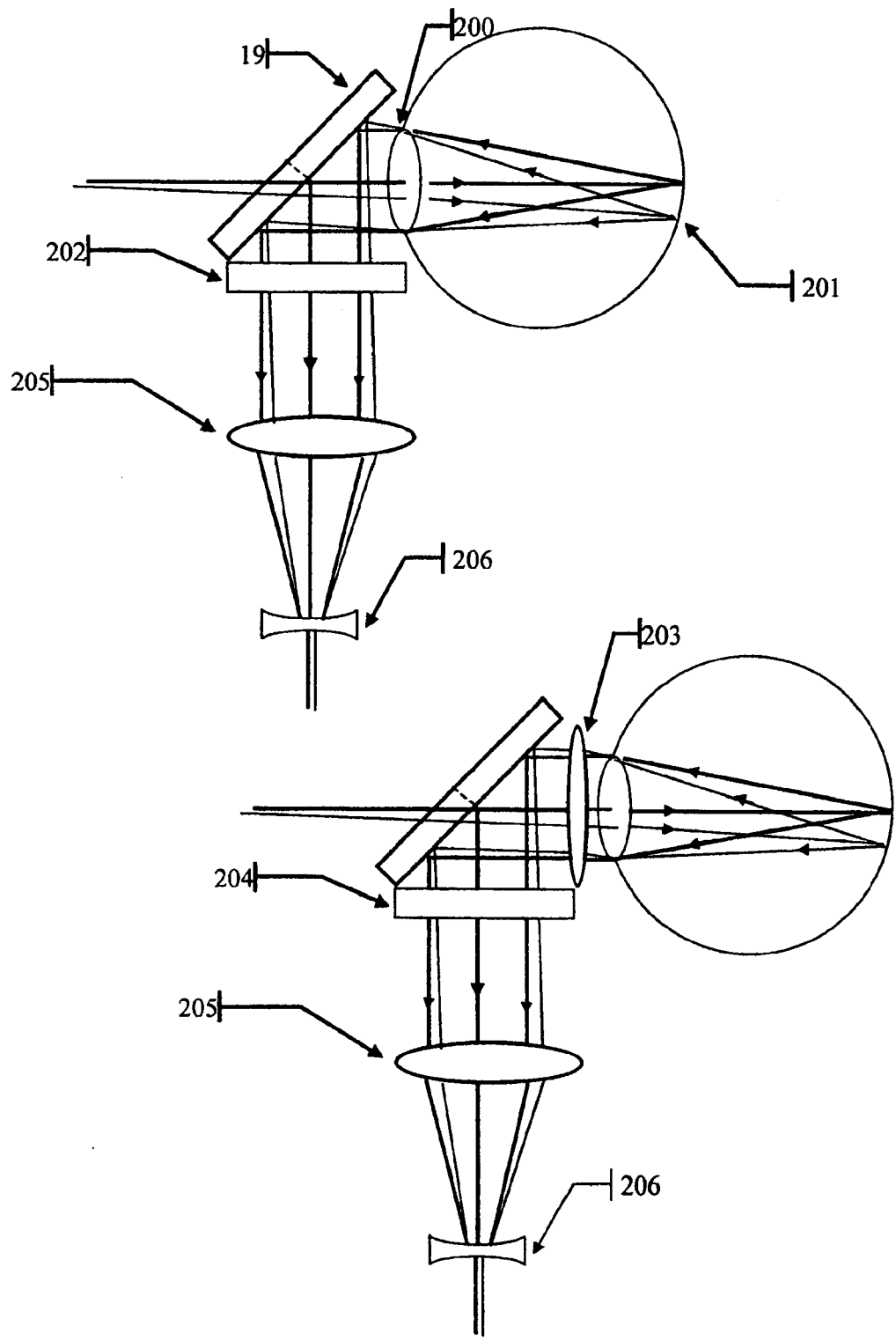
FIG. 20 shows the geometry of the impinging and exiting beams when the retina is imaged

As can be seen in FIG. 20, the back scattered photons emanating from a point 201 in the retina exit through the pupil as a conical beam; however the eye lens 200 collimates that into a parallel beam, when the patient looks at a far object. It is worthwhile to note that this conversion basically equates the path lengths along the conical beam, other than any visual aberrations the patient may have. The aberrations may be partially corrected if the patient is asked to wear his glasses 203. A more accurate correction of the path lengths may be performed by first measuring the specific aberrations of the patient's eye using wavefront analysis methods, machining a slab of lucite 204 that compensates for said aberrations and placing it on the path of the refractive beam. Lenses 205 and 206 focus and collimate the backscattered photons so that they emerge from lens 206 co-linear with the original beam reflected from the retroreflector and transmitted by the beam-splitter 19 (FIG. 1). The two beams then enter the "AND" time-Gate 24, the relative delay between the two pulses being determined by the controller 7 of the retroreflector 3. The "AND" time-Gate may be a NOLM (Non Linear Optical Loop Mirror, which is a fiber Sagnac interferometer), an optical Kerr Cell, a Second Harmonic Generating (SHG) crystal, a Two-Photon fluorescence medium (TPF), a Two-Photon Absorption (TPA) medium or a Raman-active medium. The output of the "AND" time-Gate corresponds to the overlap of the two signals in the time domain as shown in FIG. 3 by the slashed area 304. The intensity of the signal emerging from the "AND" time-Gate as detected by a fast Photomultiplier 28 is proportional to the number of backscattered photons emitted from a given layer whose depth is determined by the Z delay and its thickness by the width of the sampling signal as determined by the stretcher 6. The output of the Photomultiplier is then digitized by an Analog-to-Digital Converter 29 and stored in a memory block with its XYZ and Δ coordinates given by the controllers that control the angle of deviation of the deflector 13, the position of the mirror 15, the delay of the retroreflector 3 and the pulse stretcher 6.

Although the above narrative described the scanning of the retina in terms of orthogonal successive actions in the X, Y and Z dimensions leading to a cube of data, there is no limitation to scan any volume by defining a scan protocol limited to any volumetric shape. The only limitation is the agility of the X, Y and Z deflectors. Moreover there is no constraint to illuminate equally all areas to be imaged and the scan protocol may include for example staying in one "area of interest" more illumination time in order to gather more data there.

Figure 2:
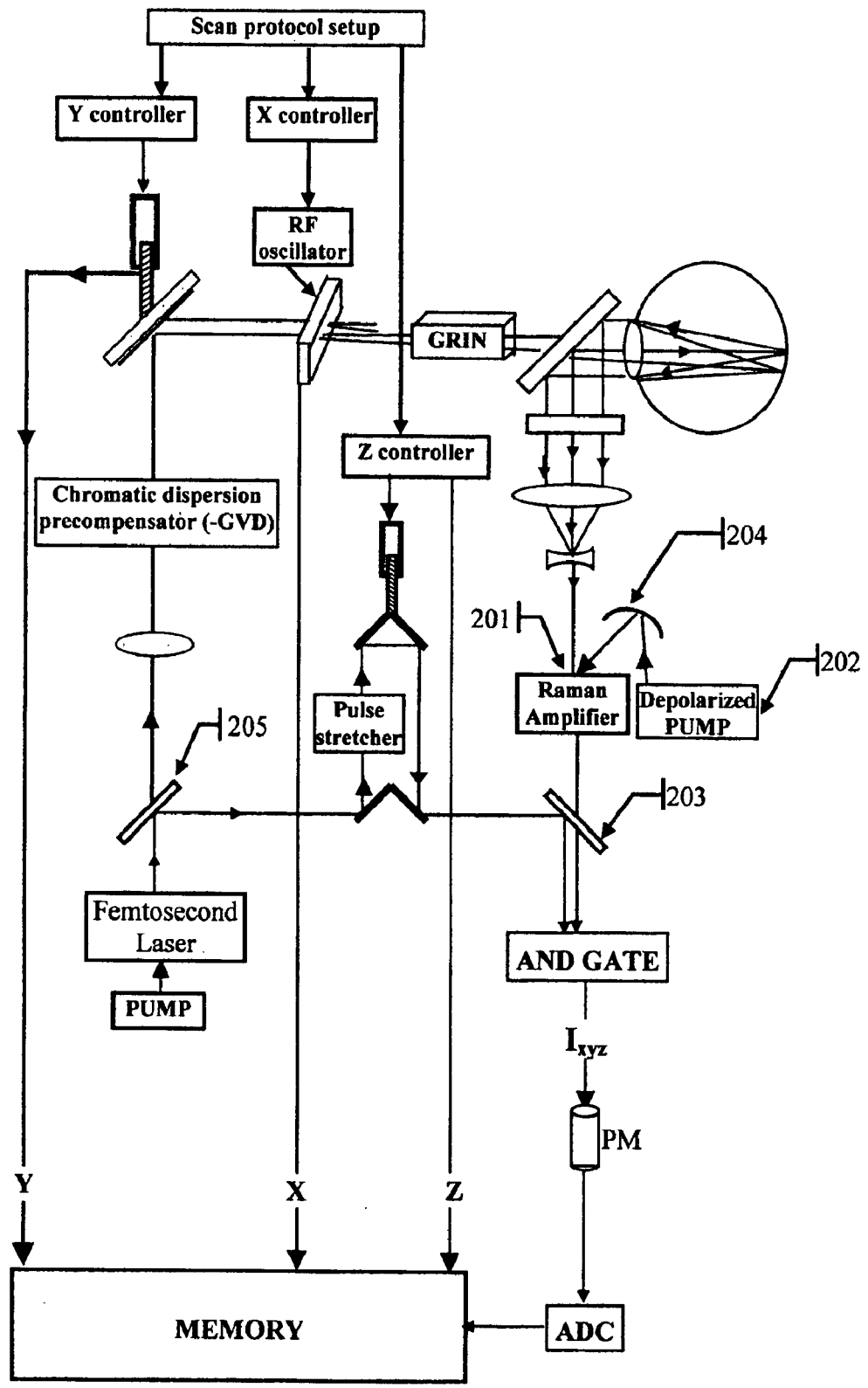
FIG. 2 shows an alternate geometry of a system for measuring the topography of a surface when the backscattered light has to be amplified without hurting the timing accuracy of the method

FIG. 2 shows an alternate geometry of the system when the signal reflected from the object is too weak to activate the "AND" time-Gate. In this case the signal is fed into a Raman-active medium 201 such as a $CaWO_4$ or $Ba(NO_3)_2$ crystal, when a higher energy (lower wavelength) pump supplies the amplification photons through the Stimulated Raman Scattering effect. To obtain maximal efficiency the pumping beam 202 and the signal to be amplified ought to be co-linear and have the same polarization angle. When the polarization of the signal to be amplified is not known the pump ought to be depolarized or two pumps with orthogonal polarizations could be used.

Figure 6:
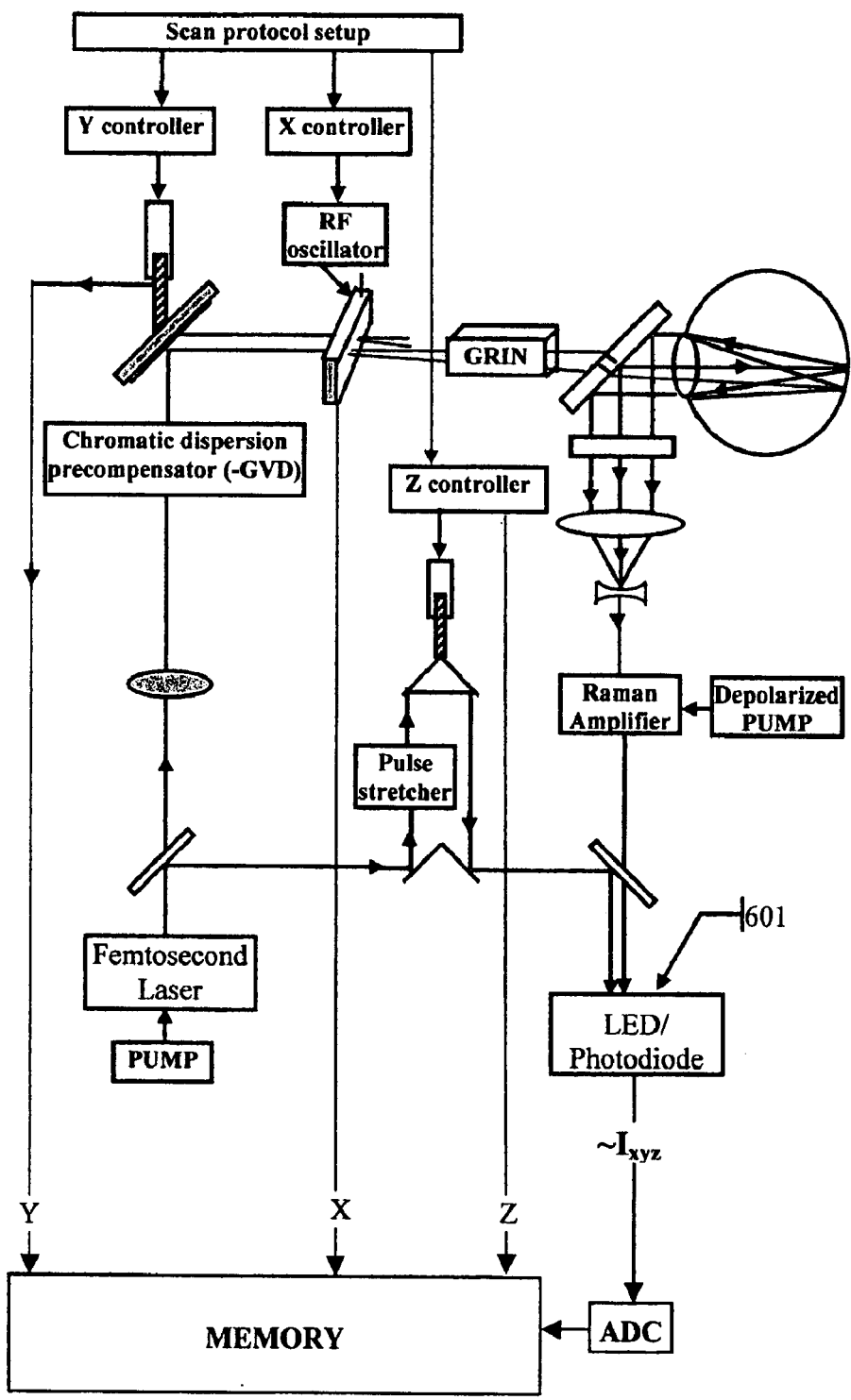
FIG. 6 shows an alternate system for measuring the topography of a surface using the time of-flight method, where the timing is measured by a LED

FIG. 6 shows a simplification of the setup of FIG. 2 where the combination of the "AND" time-Gate and Photomultiplier is replaced by a fast Photodiode or an unbiased LED 601. The Photo-diode through a Two-Photon Absorption effect generates a signal when the two signals overlap in time. Suitable Diodes are AlGaAs and InGaAs.

Figure 7:
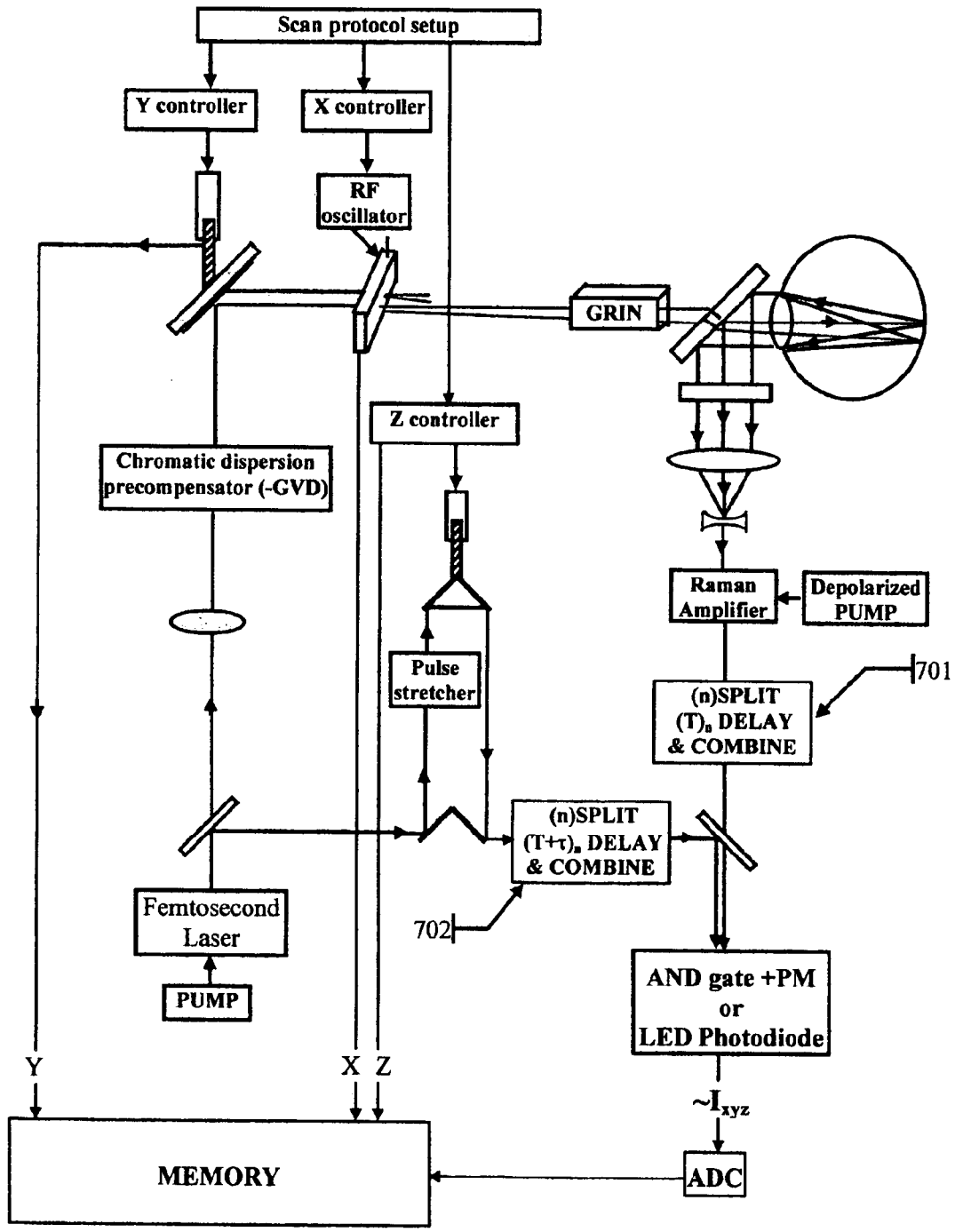
FIG. 7 illustrates a system for measuring the tomography of an object by the reflective time of-flight method using an LED to detect sequential coincidences
Figure 8:
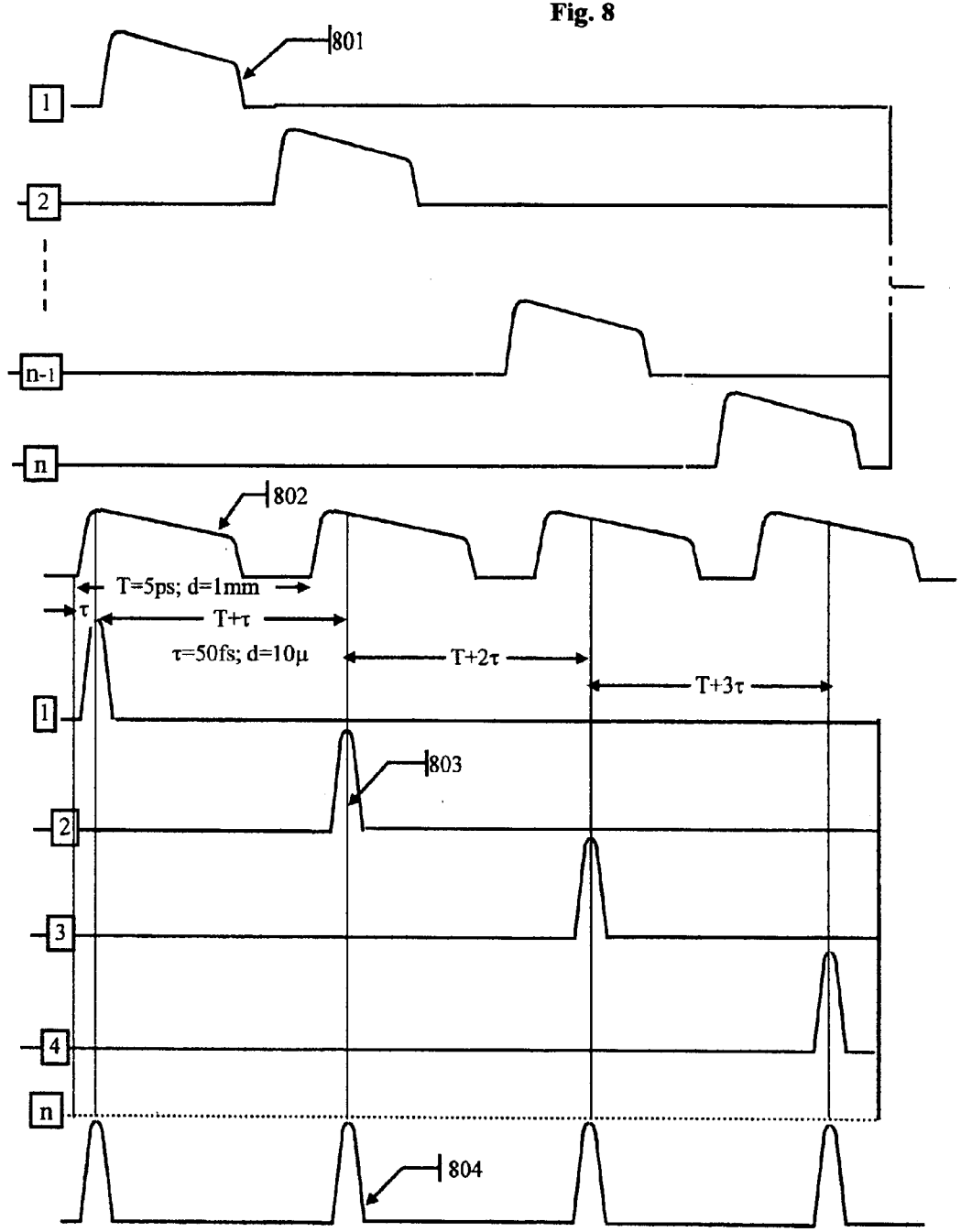
FIG. 8 illustrates the method for measuring the back-scattering intensity of all the layers in real-time, used in the system illlustrated in FIG. 7.

FIG. 7 shows a system configuration that enables to measure the intensity of the backscattered photons from all the layers of the object sequentially in real-time using a strategy that may be called the "split-delay-combine" method. In this case the backscattered signal is first amplified by a fast Raman amplifier and then split into (n) copies. As shown in FIG. 8 each (n)th copy 801 is delayed by an increasing amount nT and all the (n) copies are then combined into one serial signal 802. The total delay (nT) has to be shorter than the elapsed time between two illuminating pulses. If the back-scattered signal's duration is 4 psec. for example, the signals are delayed by (n)×(5 psec); assuming n=100 layers, the recombined chain of signals 802 will have a duration of 500 psec.

The sampling signal 702 (FIG. 7) is also split into (n) copies 803; here however each copy is delayed by (T+τ) where (τ) is equal to the width of the single layers into which it is desired to divide, the entire back-scattered signal that represents the cumulative width of all the layers. Then, all the copies of the sampling signal are combined serially into one long signal 804. The sampling pulses constituting the combined signal 804 increase in amplitude sequentially in order to compensate for the gradually weakening signals originating from the deeper layers.

When the two trains of pulses are fed co-linearly onto the AND time-Gate, the sampling signal samples the reflected signal at consecutive time slices, each of the slices representing a consecutive layer. This procedure is implemented during the time period elapsed between two consecutive illumination pulses, that illuminate adjacent pixels.

Figure 9:
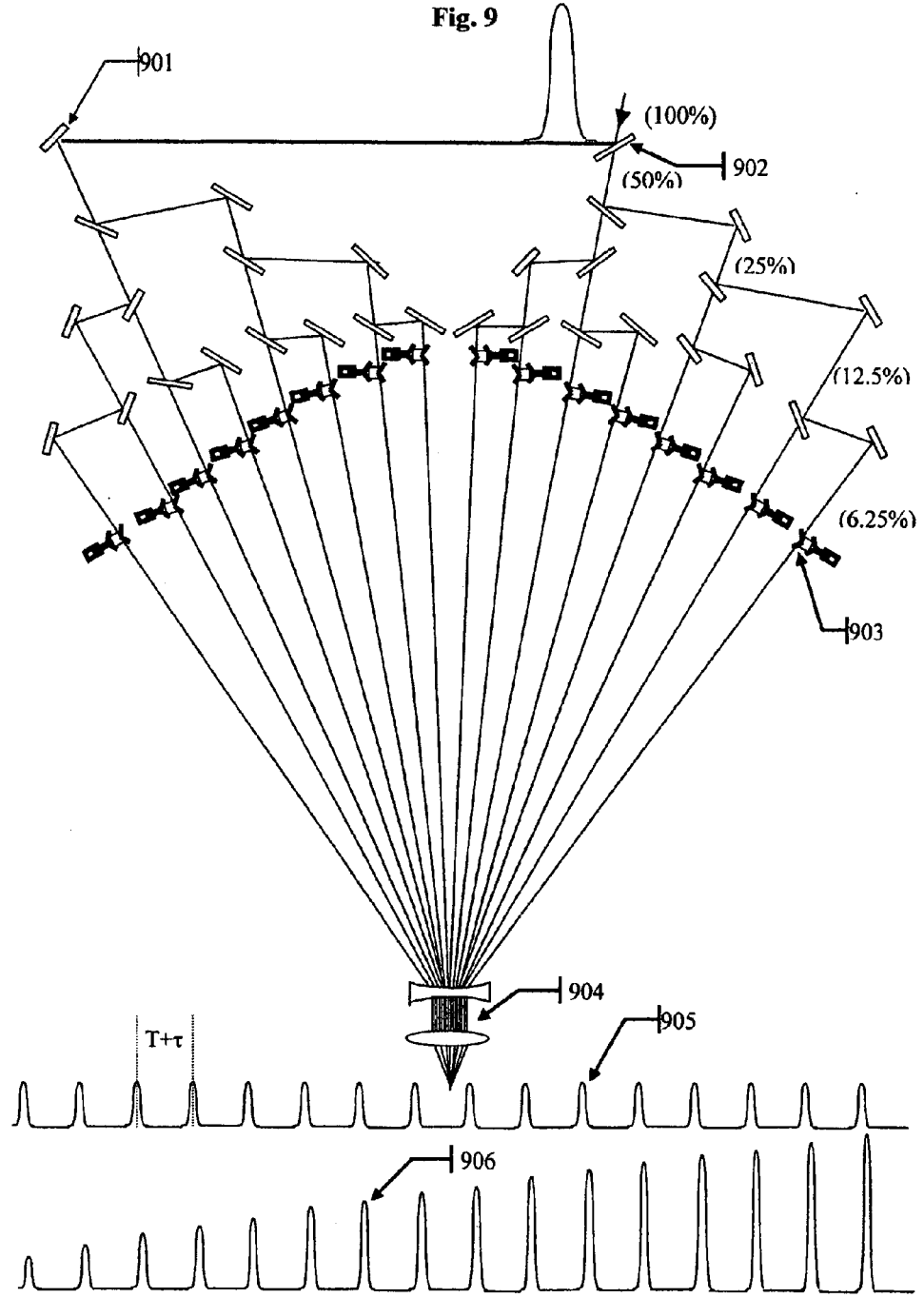
FIG. 9 illustrates a system for measuring the tomography of an object by the reflective time of-flight method using an AND time-gate to detect sequential coincidences in the time domain
Figure 10:
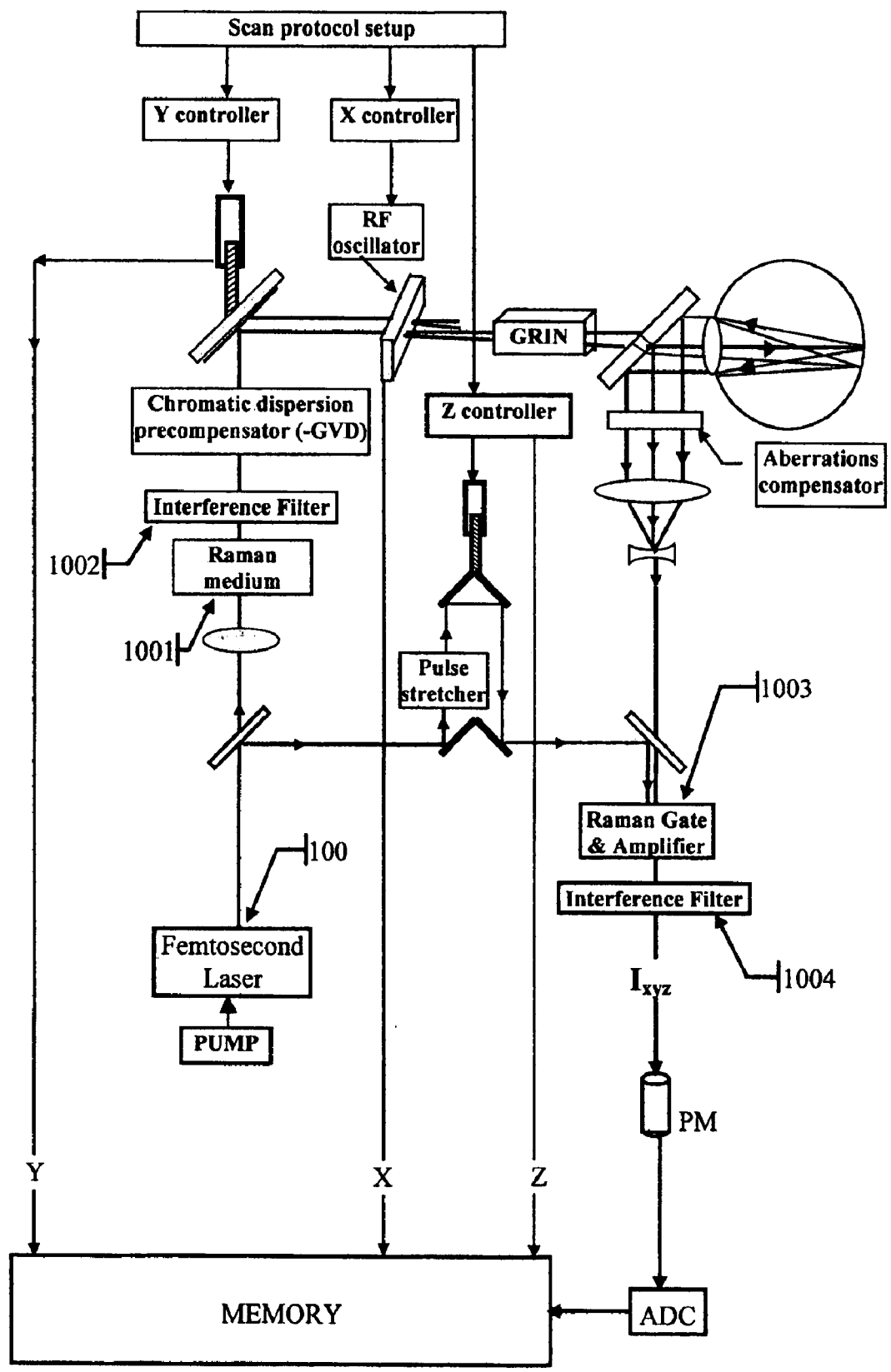
FIG. 10 illustrates a system for measuring the topography of a surface by the reflective time of-flight method using a Raman time-gate-amplifier

The splitter may actually be a passive device such as the one described in FIG. 9 and composed of fully reflecting mirrors 901 and beam-splitters 902. The temporal delay of each branch may be changed by a piezo-electric linear motor 903. Suitable optics 904 then combine the different branches onto a one long serial signal 905. The intensity of the consecutive sampling signals of the chain does not have to be uniform. By selecting different splitting ratios of the beam-splitters, the intensity of the sampling chain may be structured to increase gradually 906 in the same ratio as the expected decline of intensity of the back-scattered signal due to the absorption of the obstructing layers and the decreased solid angle of collection, thus correcting the output sample signal obtained at the exit of the AND time-gate. The splitter may also be constructed with optical fibers of selected lengths and couplers in selected ratios. The piezo-electric linear delays may be eliminated once the sampling delays are determined for a given coincidence architecture. FIG. 10 shows the system wherein the illumination beam is wavelength shifted to a Stokes beam by a Raman-active medium such as $Ba(NO_3)_2$ or $CaWO_4$ crystal and the time-gate is a completely identical Raman-active medium. The Raman-active media 1001 and 1003 are pumped in this case by the Femtolaser 1005 generating a lower energy, higher wavelength Stokes beam or amplifying it. The interference filters 1002 and 1004 filter out the original Femtolaser wavelength and the unwanted Stokes harmonics and transmit the $1^{st}$, $2^{nd}$ or $3^{rd}$ Stokes beam as desired. The weak back-scattered signal emanating from the patient's eye enters the Raman medium 1003 co-linearly with the pumping femtosecond beam and is amplified by the Stokes beam generated internally. The interference filter 1004 rejects all wavelengths but the amplified signal.

Figure 11:
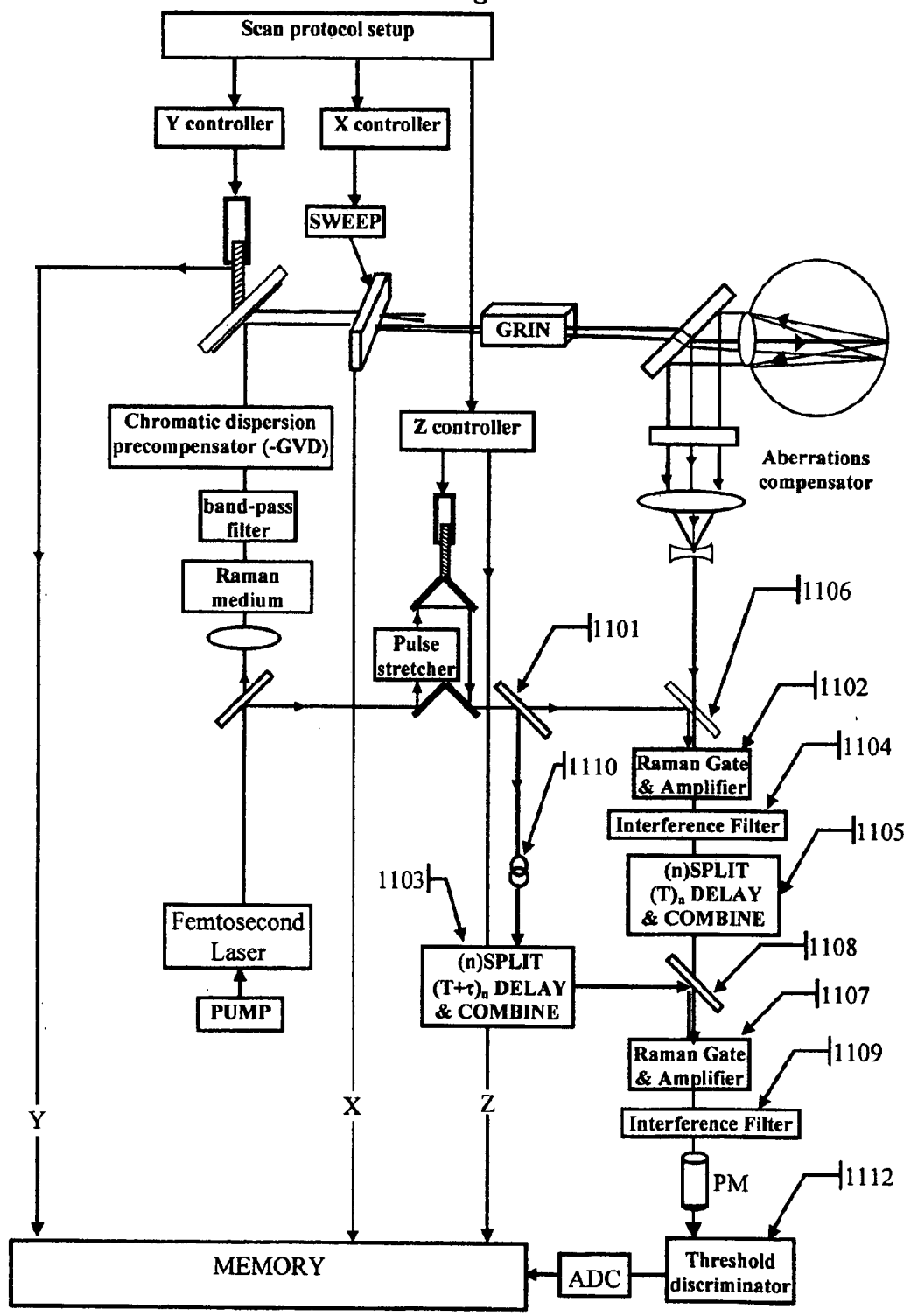
FIG. 11 illustrates a system for measuring the tomography of an object by the reflective time of-flight method using a Raman time-gate-amplifier to detect sequential coincidences in the time domain

FIG. 11 shows the same system as in FIG. 10 configured to detect all the back-scattering layers simultaneously using the "split-delay-combine" method explained above in connection with FIG. 7. The weak reflected signal from the patient's eye is first amplified by a Raman medium 1102 pumped by the Femtosecond laser beam after being split by a beamsplitter 1101, as explained above. The output of the amplifier 1102 after being filtered by the interference filter 1104 is fed into a serializing circuit 1005 that splits the signal, delays each of the components by a fixed time T and then recombines all the components into a long serial signal as explained above and illustrated in FIG. 8. This signal after being transmitted by beam-splitter 1108 is then fed co-linearly into another completely similar Raman medium 1107 together with a serialized and properly delayed signal 1103, coming from the femtosecond laser as explained above in connection with FIG. 8 and FIG. 9. The sampling pulses coming from the serializer 1003 increase in amplitude sequentially in order to compensate for the gradually weakening signals originating from the deeper layers. The strong sampling pulses coming from 1103 pump the weaker signal coming from 1105 during the time they overlap; at all other times the output of the selected Stokes frequency after the interference filter 1109 is much weaker. A fast threshold discriminator 1112 such as a saturable absorber rejects the weaker signals and transmits the amplified signals to an Analog-to-Digital Converter.

Figure 12:
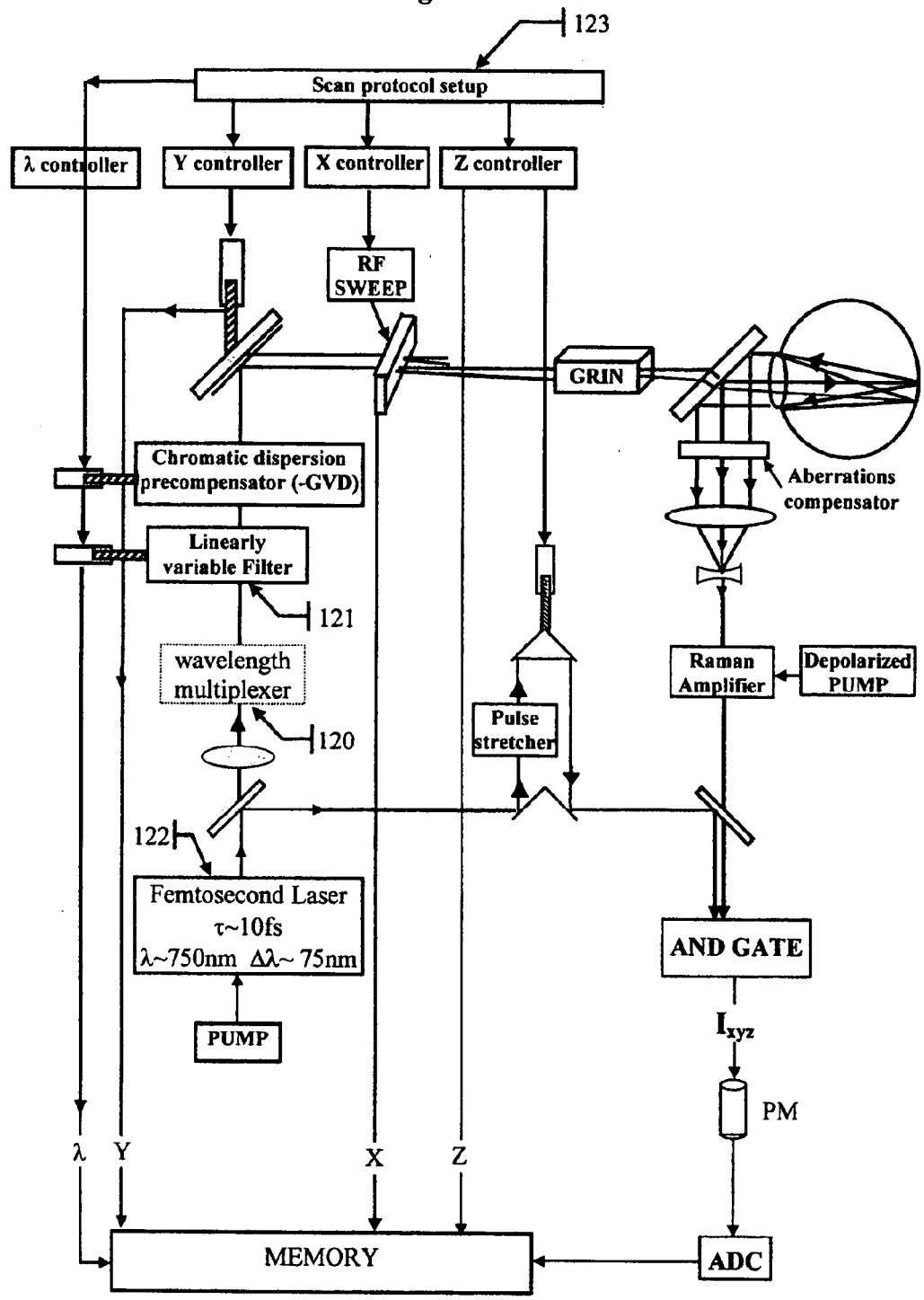
FIG. 12 illustrates a system for measuring the back-scattering intensity from a layer as a function of the illuminating beam's wavelength, by the reflective time of-flight method using an AND time-gate

FIG. 12 shows a system for obtaining the characteristics of the scattering layer as a function of the wavelength of the illuminating beam. The wavelength of the illuminating beam may be selected in several ways. One way is to use a wavelength tunable laser 122 to change the emitted wavelength and another way is to mechanically insert a linearly variable interference filter 1201 across the beam emitted by a spectrally wide laser; both of these are relatively long processes that take milliseconds and are suitable for characterizing media and processes that do not change quickly. They are useful for example for measuring oxygenation of the illuminated tissue. As the ratio of the absorption cross sections of Oxyhemoglobin and Deoxyhemoglobin at wavelengths around 810 nm and 690 nm is 1:1 and 1:7, measuring the reflected intensity at these two wavelengths will give their relative ratio. The system is therefore configured so that the femtosecond laser 122 is tuned at a frequency around 750 nm and a femtosecond laser of short pulse-width of around 10 fs is selected so that its spectral bandwidth is $\Delta\omega=10\%$ ($\omega$)=75 nm. Thus the linearly variable filter 121 can be positioned by the piezoelectric motor, at ~700 nm and ~800 nm sequentially to change the transmitted bandwidth every several milliseconds. The scan protocol controller 123 determines the sequence of illumination of the area of interest at different wavelengths. However if the object being measured changes quickly, it is advantageous to measure its characteristics as a function of wavelength rather quickly, if possible simultaneously.

Figure 13:
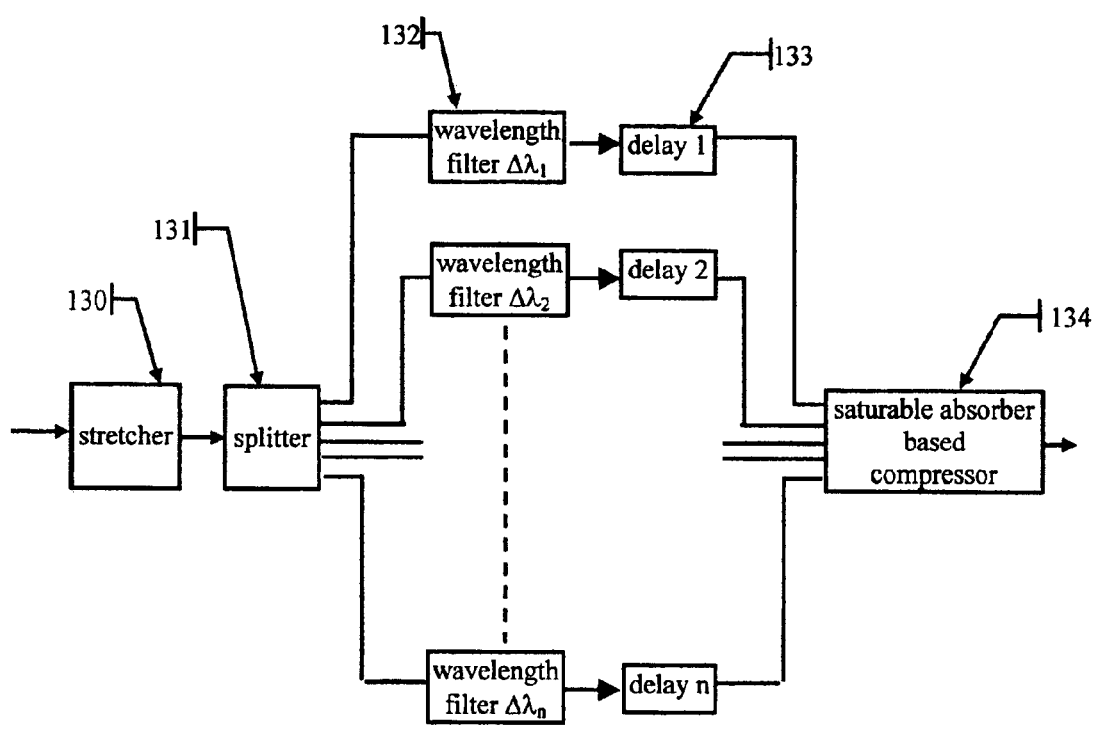
FIG. 13 illustrates a method for generating a series of femtosecond pulses at different wavelengths using the ultrashort femtosecond pulse

FIG. 13 illustrates a "wavelength multiplexer", a method of generating a series of femtosecond pulses at different wavelengths using the ultrashort femtosecond pulse. The ultrashort femtosecond pulse is passed through a variable stretcher 130 based on double gratings, for spectrally broadening it. A splitter 131 divides said spectrally broadened pulse into several branches; interference filters 132 then transmit a selected wavelength in each branch. Each wavelength filtered branch is delayed 133 by an increased amount, and combined with the other increasingly delayed wavelength filtered branches, thus creating a sequence of temporally separated light pulses, each of a different wavelength. The recombined signal line is then passed through a saturable absorber based pulse-width compressor 134 that recompresses the pulses of the different wavelengths(see U.S. Pat. No. 6,356,693 semiconductor optical pulse compression waveguide by Shimazu).

Figure 14:
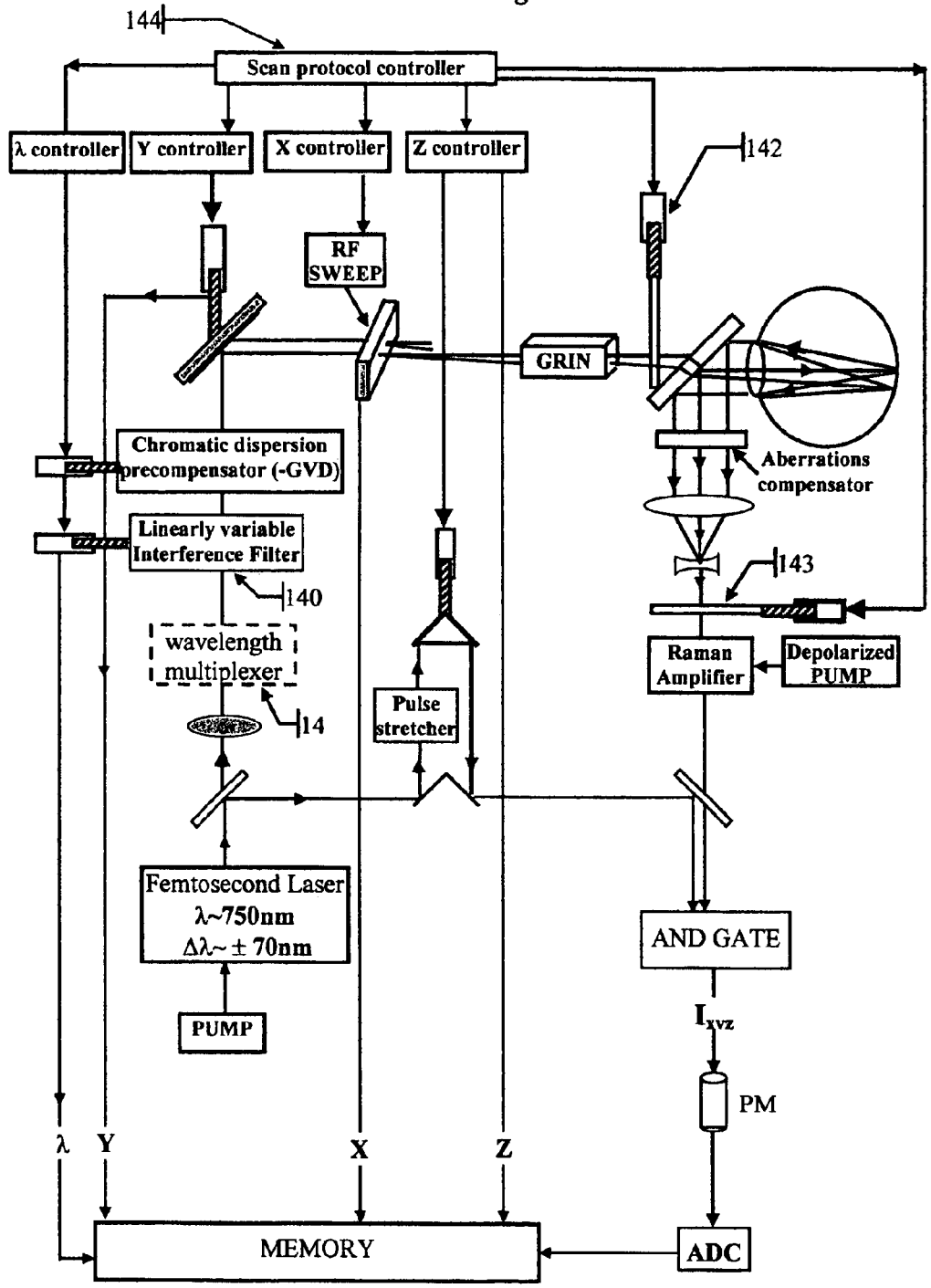
FIG. 14 illustrates the rejection of multiple-scattered photons by eliminating photons with a polarization different than the once-back-scattered photons, in a system for measuring the intensity of back-scattering from a layer as a function of the illuminating beam's wavelength.

FIG. 14 shows the measurement of the change of polarization of the reflecting body. A rotatable polarizing medium 142 such as a Pockels cell or a quarter wavelength plate controlled by the master scan protocol controller 144 is inserted across the illuminating beam so as to establish a given polarization angle. The polarization analyzing medium 143 is properly placed so as to detect only the once backscattered photons. This can be achieved by calibrating the system with a phantom scatterer that has only one layer of scattering material close in composition to that of the body to be measured and strongly limiting the solid angle of detection. Thus the properly positioned polarization analyzing medium 1302 will strongly reduce the intensity of the multiple scattered photons that still are within the time window of the AND time-Gate.

Figure 15:
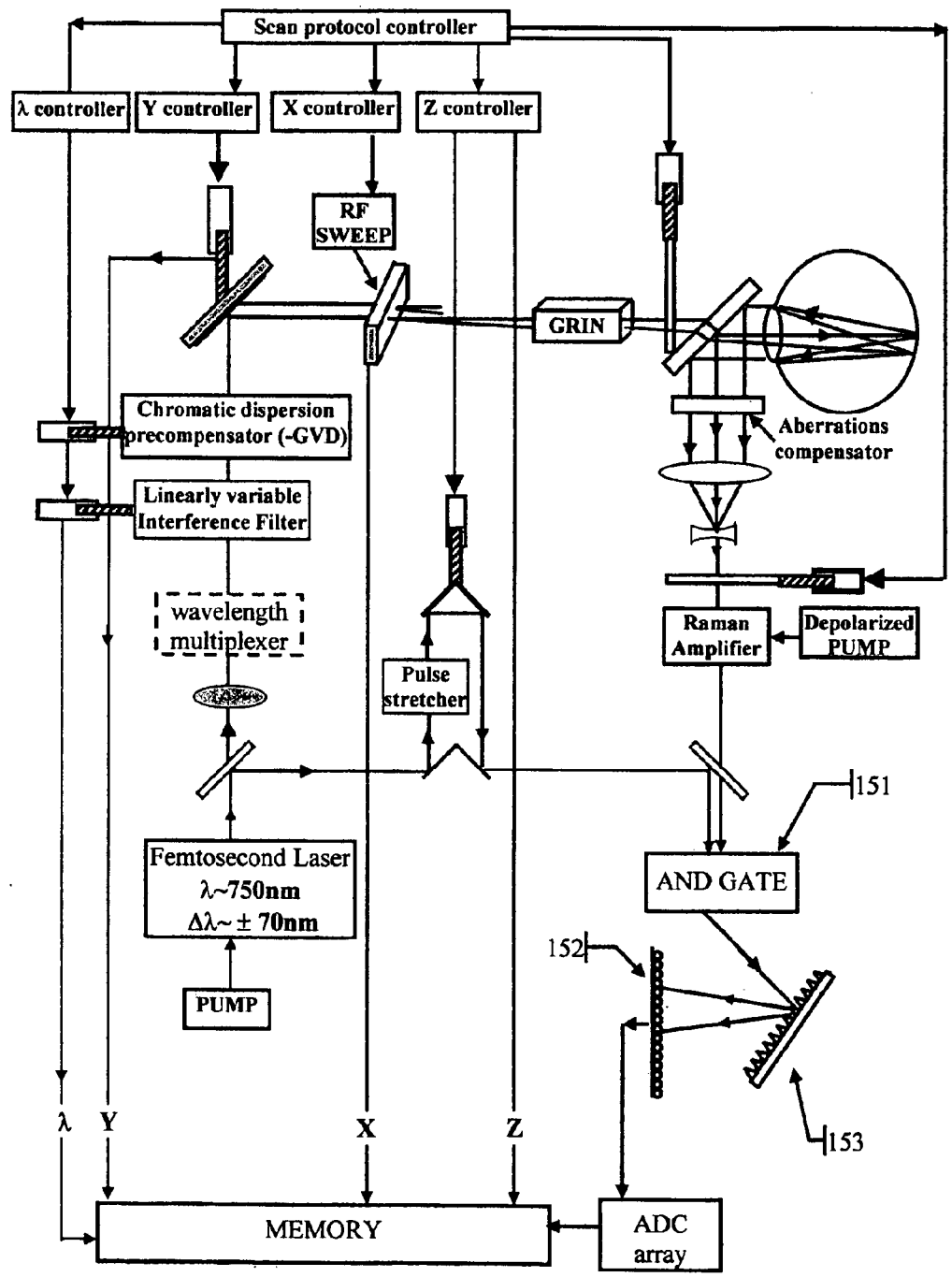
FIG. 15 illustrates a system for measuring the non-elastic back-scattering intensity from a layer as a function of the emitted wavelengths.

FIG. 15 shows the measurement of the spectral composition of the back-scattered photons due either to a change of the wavelength of the illuminating beam or due to inelastic scattering and fluorescence of the emitting layer, after being amplified by a broadband Raman amplifier 140 that having a given spectral response has to be taken into account when deriving the original spectrum. The spectrum of the AND time-gate output which is a function of the incoming spectra, is analyzed on the fly by a spectrometer composed of a grating 143 and a fast linear array of photo-detectors 142 whose outputs are digitized in parallel by an ADC array. Thus after applying the corrections due to the Raman amplification and the AND time-gate response that is different for the specific medium used, it is possible to get on a pixel-by-pixel basis the spectrum of the emitted radiation that will show the absorption bands and fluorescence of the illuminated body.

Figure 16:
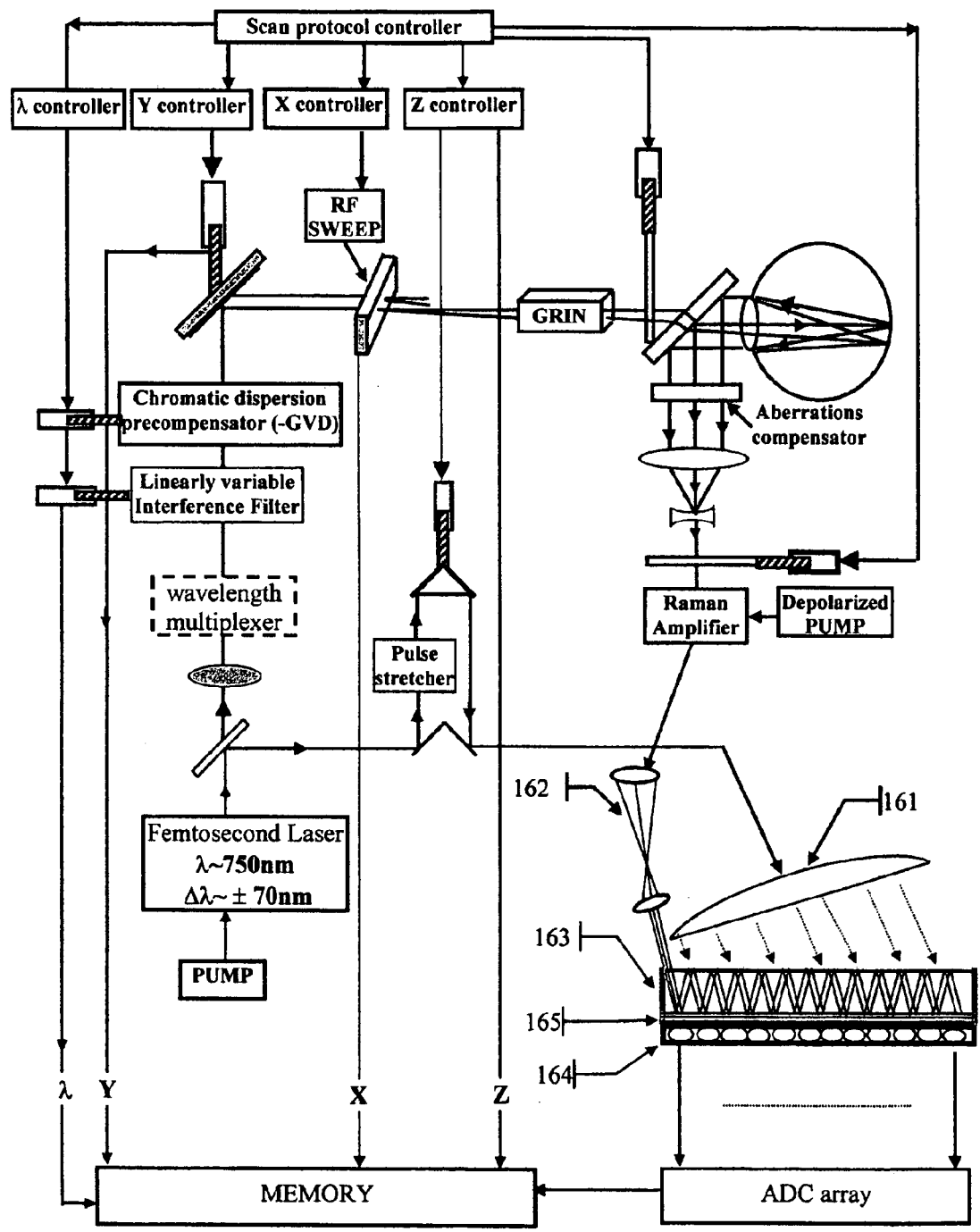
FIG. 16 illustrates a system for measuring the back-scattering intensity from a multiplicity of layers using a continuous chain of linked AND time-gates
Figure 17:
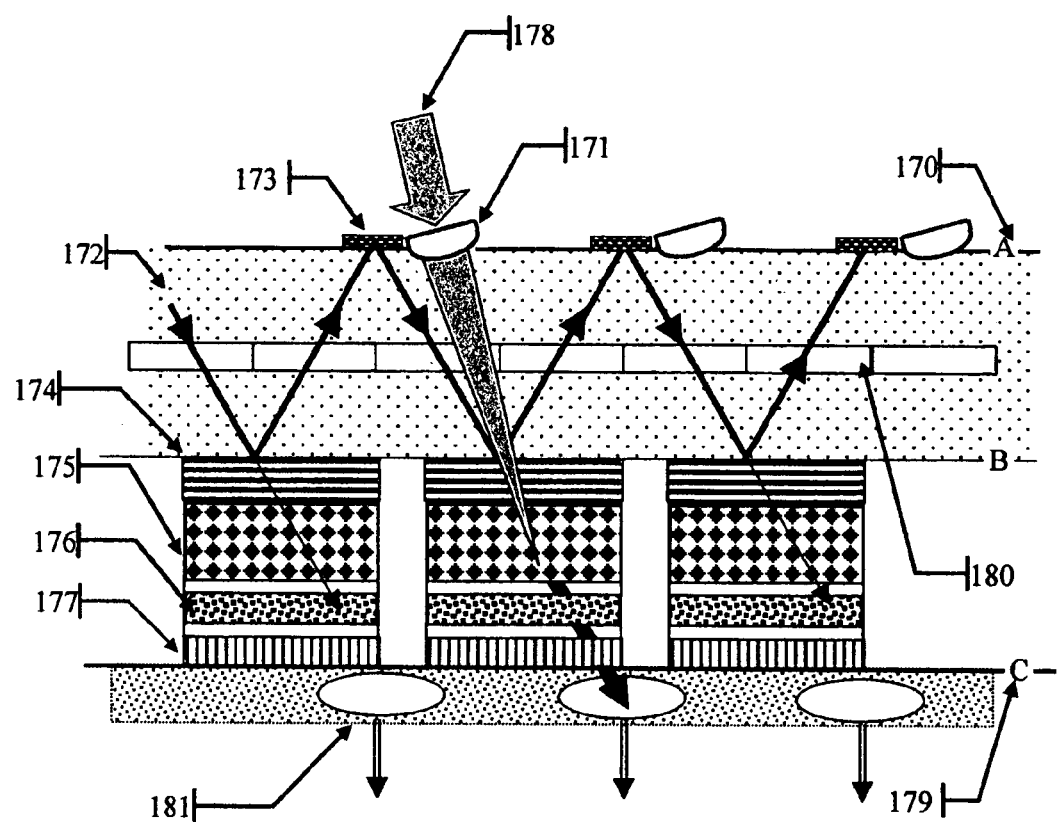
FIG. 17 shows a common structure for a chain of linked SHG, Two Photon Absorption or Raman "AND" time-gates

FIG. 16 shows an alternate way to measure the shape and intensity of the backscattered pulse that represents the cumulative scattering response of all the layers. The analog signal representing the backscattered light is first amplified by a fast Raman amplifier. The output from the amplifier is shaped into a narrow collimated beam by suitable optics 162 that direct the beam at one of the plates 165 of the "analog serial-to-parallel converter" 163 consisting of a chain of linked, non-linear, optical analog AND time-gates. As illustrated in FIG. 17, the chain of linked analog AND time-gates may be implemented by two closely spaced parallel transparent plates A and C, 170 and 171, between which the analog signal 172 entering the space between the mirrored plates at a preselected angle, propagates, reflected from one plate to another. The top plate 170 is coated with a fully reflective chirped dielectric mirror 173 having a Negative Group Velocity Dispersion. The bottom plate 171 a bottom plate has a four layer coating as follows:

a) an upper dielectric mirror 174 reflecting a substantial portion of the impinging analog signal, and transmitting a small portion of it to the next layer b) a layer of a non-linear crystalline material 175 that may be either an SHG crystal, a Two-Photon Fluorescence medium, or a Raman-active crystal, beneath the dielectric mirror, where the non-linear interaction between the analog signal 172 and the sampling signal 178 takes place, c) a saturable absorber 176 beneath the non-linear crystalline material that absorbs the weak, analog signal transmitted through the dielectric mirror and did not interact within the crystalline material, d) an interference filter 177 that transmits only the sampled wavelength resulting from the interaction between the analog signal and the sampling pulse and absorbs or reflects all other wavelengths Alternatively a solid, rectangular slab of material, transparent to the wavelengths of the signal and sampling beams, may be used, and the opposite faces (A) 170 and (B) 179 coated from the outside in the same manner described above. In case two separate plates are used, a lenslet array 180 made of GRIN (GRadient INdex) material, may be inserted in between the plates in order to refocus the signal beam that tends to diverge between reflections as shown in FIG. 19. In order to focus strongly the sampling beam onto a small region (<10 μm) of the material where the non-linear interaction between the two beams takes place, objective lenses 171 with high N.A. are inserted onto the upper plate, where the sampling beam 178 enters the device.

If the non-linear medium is an SHG crystal or a TPA semiconductor the interaction between the analog and the sampling signals will generate photons having the sum energy of the interacting beams. If the crystal is a Raman-active medium, the higher energy sampling beam will amplify the lower energy analog signal through the Stimulated Raman Scattering (SRS) process. The analog signal that did not interact with the sampling signal is absorbed by the layer of the saturable absorber, while the residual of the sampling beam is absorbed by the interference filter that transmits only the amplified signal wavelength in case the non-linear crystal is a Raman-active medium or the sum-energy photons in case the non-linear crystal is an SHG or TPA crystal. The signal exiting the interference filter is detected by a detector of the photo-detector array 181.

Figure 18:
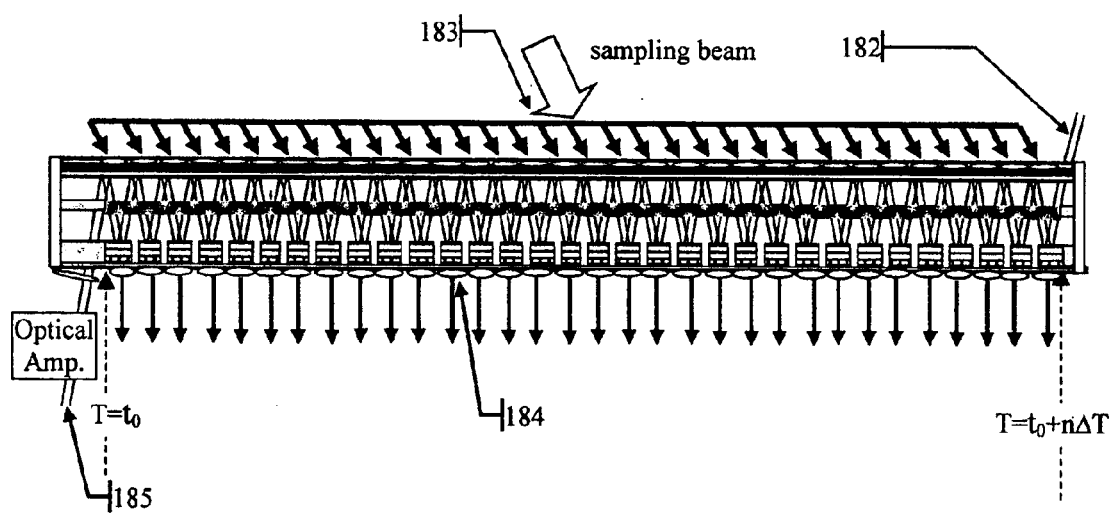
FIG. 18 shows the structure of a continuous chain of 32 AND gates

FIG. 18 illustrates a chain of 32 linked AND time-gates, where an analog signal 185 may be sampled in real time by a sampling beam 183 in parallel. The sampled signal detected by the (n)th Photo-detector 184 gives the intensity of the scattered light from the slice nΔT of the analog signal representing the intensity of light emitted by the (n)th layer. This signal has to be corrected for the attenuation experienced when reflected from one AND time-gate to the next by calibrating the device with a flat same-intensity signal and applying the measured attenuation in each AND time-gate to the detected signal exiting said AND time-gate, to correct the shape of the sampled analog signal.

Changing the distance between the plates enables to adjust the thickness of the layer observed. Changing the relative inclination of the plates results in gradually increasing the layer's thickness, which may be desirable in certain instances.

The precise time of gating the device by the sampling pulse may be adjusted by changing the relative delay and synchronized to the moment when the analog signal occupies the entire length of the device.

FIG. 19 illustrates the spatial dispersion experienced by the reflected analog signal when reflected from one plate to another. Such spatial dispersion may be corrected by placing a miniaturized array of properly inclined lenslets 193 between the two opposite plates so as to focus the reflected beam back onto the opposite plate. The lenslet array may also be constructed of GRaded Ibdex (GRIN) material 198. In order to prevent cross-talk between adjacent areas physical stops 192 are placed between time-gates..

FIG. 20 shows the geometry of the impinging and exiting beams when the retina is imaged, the specifics of which were discussed in the context of the system illustrated in FIG. 1.

I claim:

1. An apparatus for determining the tomography of a volume of an object by
    a) illuminating the object with a temporally ultrashort pulse of light having a preselected temporal width, corresponding to a narrow range of wavelengths penetrating said object, and
    b) determining the spatial coordinates of a voxel, at the surface or within the object, by measuring the time-of-flight from the pulsed source of light to said voxel defined by the cross-section of the impinging pulse of light and the thickness of the voxel defined by the temporal width of the pulse of light,
    c) measuring the intensity of the interaction between the impinging pulse of light and the matter within said small voxel, by measuring the intensity of the scattered light as a function of the wavelength of the impinging pulse of light and spectrum of the detected pulse of light, within the elapsed time between two consecutive pulses of light and
    d) determining the position and scattering intensity of all axially adjoining voxels in the direction of the impinging pulse of light, in the Z direction, by sorting all scattered light photons according to their time-of-flight, within the elapsed time between two consecutive pulses of light and e) scanning the desired volume of the object transversally in the X and Y directions by deflecting the light beam from one set of axially adjoined Z voxels in the direction of the impinging pulse of light, to an adjacent set of axially adjoined Z voxels in the direction of the impinging pulse of light, comprising (i) A femtolaser generating a first ultrashort light pulse divided by a beamsplitter or optical coupler in unequal proportions into mutually coherent second and third ultrashort light pulses, directing the second ultrashort light pulse to the small voxel whose distance is to be measured and the third ultrashort light pulse to an AND time-gate, said unequal proportions determined experimentally as the proportion that maximizes the signal-to-noise ratio at the output of the AND time-gate, and (ii) means for monitoring the intensity of each ultrashort pulse illuminating the object (iii) means disposed between the second light pulse and the object, to process and shape said second light pulse geometrically, temporally, spectrally and polarization-wise, before it interacts with matter in said voxel of the object, and (iv) means disposed between the third ultrashort light pulse and the AND time-gate, to process geometrically, spectrally and polarization-wise said ultrashort light beam, before it interacts with said time-gate, and (v) means for collecting the backscattered light following the interactions between said processed second light pulse and the voxels along the cross-section of the object penetrated by said processed second light pulse, as a function of the backscattering angle, and (vi) means for amplifying and processing said collected back-scattered light pulse temporally, spectrally and polarization-wise and directing it to the AND time-gate, collinearly with the said coherent, processed third ultrashort light pulse, (vii) means disposed between said processed third ultrashort light pulse and said AND time-gate for varying the transit time of said third ultrashort light pulse and its pulsewidth, to cause said processed third ultrashort light pulse to temporally and geometrically overlap with selected temporal sections of the collected back-scattered light pulse at said AND time-gate, and (viii) a wavelength filter or grating for spatially separating the spectral components of the light pulse exiting the AND time-gate, and (ix) means for sampling in real-time the temporal intensity of each of the spectral components of the amplified back-scattered light pulse exiting the AND time-gate, each adjacent sample denoting the intensity of the back-scattered light of a specific wavelength, emitted from an adjacent voxel of the object along the path penetrated by the processed second light pulse, and (x) means for sampling in real-time the temporal intensity of each of the spectral components of the amplified back-scattered light pulse exiting the AND time-gate, as a function of the wavelength of the processed second light pulse impinging on the object, each temporally adjacent sample denoting the intensity of the back-scattered light of a specific wavelength emitted from an axially adjacent voxel of the object, along the path penetrated by the processed second light pulse of a specific wavelength, and (xi) Analog-to-Digital Converters for digitizing in parallel the light intensity for each sample in the time domain as a function of the wavelength of the processed second light pulse impinging on the object and the wavelength of the processed back-scattered light pulse, and normalizing said intensity by dividing it by the intensity of the first pulse of light, and (xii) means for deflecting the light beam continuously from one position to another transversal position within the time elapsed between two consecutive light pulses, comprising two acousto-optical deflectors operating orthogonally and placed at a distance from the object so that their small angular apertures cover the desired span of the surface to be scanned and (xiii) means for raster scanning a surface by deflecting the light beam continuously along an arc of a circle or a straight line and then to an adjacent arc of a circle or a straight line and (xiv) means for synchronizing the beam deflectors (xii) and (xiii) with the laser pulse rate, and (xv) multi-dimensional storage means for storing the normalized intensity of the backscattered light from each voxel along the axial and transversal directions as a function of the impinging light's wavelength, the scattered light's wavelength and the backscattered angle.

2. The apparatus of claim 1 wherein the laser generating a first temporally ultrashort light pulse, is a wavelength tunable laser or a multi-wavelength laser.

3. The apparatus as in claim 1 wherein means disposed between the second light pulse and the object, to process and shape said light beam geometrically, comprise focusing and collimating optics including GRaded INdex (GRIN) lenses and physical limiters to collimate the beam, narrow its cross section to the desired dimensions and compensate for the axial temporal dispersion across the cross section of the beam.

4. The apparatus as in claim 1 wherein means disposed between the second light pulse and the object, to process and shape said light beam temporally, include a grating or prism based variable compressor for compensating for the pulse-width broadening expected along the path until the light pulse reaches the voxel whose distance is to be measured.

5. The apparatus as in claim 1 wherein means disposed between the second light pulse and the object, to process and shape said light beam temporally and spectrally, include a grating or prism based variable stretcher for spectrally broadening the second light pulse, a beamsplitter for splitting said spectrally broadened second light pulse into several branches, interference filters that transmit a selected wavelength in each branch, delay means that delay each of the wavelength filtered branch by an increased amount, and a combiner that combines said increasingly delayed wavelength filtered branches, a compressor that compresses the pulses of different wavelengths, thus creating a sequence of temporally separated ultrashort light pulses, each of a different wavelength.

6. The apparatus as in claim 1 wherein means disposed between the second light pulse and the object, to process and shape said light beam spectrally, include mechanically insertable wavelength filters that select the wavelength of the light pulse impinging on the object.

7. The apparatus as in claim 1 wherein means disposed between the second light pulse and the object, to process and shape said light beam spectrally include a Raman-active medium, such as a Barium Nitrate $(BaNO_3)_2$ or a Calcium tungstate $(CaWO_4)$ crystal where the second light pulse is wavelength shifted to a preselected Stokes wavelength to produce a Stokes light pulse and a wavelength filter that transmits only the selected Stokes wavelength and eliminates all light of different wavelengths.

8. The apparatus as in claim 1 wherein means disposed between the second light pulse and the object, to process said light beam polarization-wise, include a Pockels cell or a quarter-wavelength waveplate that linearly polarizes the beam impinging on the object and means disposed between the back-scattered light pulse and the AND time-gate include a polarization analyzer that differentiates by their polarization angle between the once back-scattered light and multiple-scattered light that reaches the optics collecting the back-scattered light, transmits only the once back-scattered light and eliminates all other light components that have a different polarization and means disposed between the third light pulse and the AND time gate include a Pockels cell or a quarter wavelength plate that rotates the polarization angle of the of the third light pulse so as to make it parallel to that of the processed back-scattered light pulse before it enters the AND time-gate.

9. The apparatus of claim 1 wherein the AND time-gate is an SHG (second Harmonic Generation) crystal such as a KDP, KTP or BBO crystal, a photodetector having a band-gap larger than the energies of either the second or third light pulses but slightly smaller than the sum of the two such as an InGaAs or AlGaAs LED in respect to a 800 nm illuminating pulse of light, or a Raman amplifier consisting of a Raman-active medium completely identical to the Raman-active medium that may have been introduced to shift the wavelength of the second light pulse, followed by a thresholding saturable absorber and a band-pass wavelength filter that transmits only the band of wavelengths included in the back-scattered light and eliminates all light of different wavelengths.

10. The apparatus as in claim 1 wherein means for collecting the backscattered light comprise wide-angle optics that collect, focus and collimate the back-scattered light, including mechanically translatable annular lenses around the axis of the impinging second light pulse, to collect backscattered light at angles smaller than 180°, and direct such back-scattered light into the AND time-gate.

11. The apparatus as in claim 1 wherein means for amplifying said collected processed back-scattered light pulse include an ultrafast optical amplifier that does not negatively impact the rise-time of the processed back-scattered light pulse, such as a Raman amplifier.

12. The apparatus as in claim 1 wherein means for temporally processing said back-scattered light pulse include, GRaded INdex lenses that compensate for the temporal dispersion due to the conical geometry of the back-scattered light and aberrations introduced by the medium between the scattering voxel and the light collecting optics.

13. The apparatus as in claim 1 wherein means disposed between the third ultrashort light pulse and the AND time-gate includes optics that focus and collimate the light pulse and direct it to the AND time-gate collinearly with the processed back-scattered light.

14. The apparatus as in claim 1 wherein means disposed between the third ultrashort light pulse and the AND time-gate, include a grating or prism based variable compressor/stretcher that introduces, either a negative group velocity dispersion for compensating for the expected pulse-width broadening, or a positive group velocity dispersion for broadening the pulse width, so as to expand the temporal range within which said third ultrashort light pulse is in coincidence with the processed back-scattered beam.

15. The apparatus as in claim 1 wherein means for scanning an arc of a circle or a straight line by deflecting the light beam continuously along said arc of a circle or straight line, within the time elapsed between two consecutive light pulses, comprises a reflective mirror coating attached to the tip of a vibrating piezoelectric bimorph cantilever, that deflects the scanning laser beam, such deflection amplified by reflecting the deflected beam by a pair of confocal focusing mirrors placed at an acute angle.

16. An apparatus as in claim 1 for imaging the retina of the eye wherein (i) the femtolaser generating a first ultrashort light pulse is a mode-locked laser emitting pulses less than 20 femtoseconds wide, at a wavelength between 700 nm and 800 nm, having a power higher than 10 mW, and at a repetition rate of more than 10 MHz (ii) a beamsplitter that splits the first light pulse in such a proportion that the power of the second light beam that is directed towards the retina is less than 1 mW and the rest is apportioned to the third light pulse (iii) means disposed between the second light pulse and the retina, to include; a stretcher to expand the pulse up to 500 femtoseconds, a splitter to split said stretched pulse in two, two interference filters centered at 700±10 nm and 800±10 nm inserted in each of the branches, one of the branches delayed by 1 nsec, a combiner that recombines the delayed and filtered branches and a pulse width compressor that recompresses the two temporally 1 nsec apart pulses.

17. A method for sampling an ultrafast optical analog signal in the time domain that consists in (i) propagating the analog signal to be sampled through a chain of linked, non-linear, optical analog AND time-gates, such analog AND time-gates, in the absence of a strong gate pulse, being transparent to the transmission of a controlled substantial portion of the analog signal from one analog AND gate to the next; the propagation time within the analog AND time-gate, being equal to the length of the analog signal to be sampled in the time domain, divided by the number of linked analog AND time-gates and (ii) applying a strong gating pulse of light to the chain of linked analog AND time-gates simultaneously, for a duration of the desired sampling time, causing the generation of a sample signal output as a result of the interaction between the analog signal and the gating pulse of light, such sample signal output being proportional to the momentary intensity of the analog signal traversing the analog AND time-gate at that time, (iii) eliminating the portions of the analog signal and the gating pulse of light that did not interact, from the sample signal output, (iv) digitizing the sampled signals from each analog AND time-gate separately (v) correcting for the attenuation of the analog signal between the analog AND time-gates.

18. An apparatus according to the method outlined in claim 17 wherein the chain of linked analog AND time-gates consists of two closely spaced transparent plates, said plates being parallel or at a relative inclination one in respect of the second, between which the analog signal entering the space between the mirrored plates at a preselected angle, propagates reflected from one plate to another and comprising:

(i) a top plate coated with a fully reflective chirped dielectric mirror having a Negative Group Velocity Dispersion (ii) a bottom plate having a four layer coating as follows:

d) an upper dielectric mirror reflecting a substantial portion of the impinging analog signal, and transmitting a small portion of the impinging analog signal to the next layer e) a layer of a Raman-active medium beneath the dielectric mirror that amplifies the analog signal when in temporal coincidence with a strong pulse at a Stokes wavelength f) a saturable absorber beneath the Raman-active medium that absorbs the weak, non-amplified analog signal transmitted through the dielectric mirror g) an interference filter that transmits only the sampled wavelength and absorbs the gating Stokes pulse (iii) a linear array of lenslets positioned between the two plates for refocusing the analog signal beam reflected between the dielectric mirrors of the two plates (iii) a strong light pulse source at a shifted Stokes wavelength from the analog signal, serving as the gating pulse for the analog signal that propagates by reflection between the two plates, applied across the top plate, directed towards the bottom plate and strongly focused on the Raman-active medium beneath the area from where the analog signal is reflected, (iii) a preferably Avalanche Photo-Diode array placed immediately underneath the interference filter where the amplified sampled signals are collected.

19. An apparatus according to the method outlined in claim 17 wherein the chain of linked analog AND time-gates consists of two closely spaced parallel transparent plates, said plates being parallel or at a relative inclination one in respect of the second, between which the analog signal entering the space between the mirrored plates at a preselected angle, propagates reflected from one plate to another and comprising:

(iii) a top plate coated with a fully reflective chirped dielectric mirror having a Negative Group Velocity Dispersion (iv) a bottom plate having a three layer coating as follows:

h) an upper dielectric mirror reflecting a substantial portion of the impinging analog signal, and transmitting a small portion of the impinging analog signal to the next layer i) a layer of a crystalline medium such as an SHG crystal or a TPA medium beneath the dielectric mirror that generates a signal of the sum of their energies when swept by two signals in temporal coincidence j) an interference filter that transmits only the sum energy light (iii) a linear array of lenslets positioned between the two plates for refocusing the analog signal beam reflected between the dielectric mirrors of the two plates (iii) a strong light pulse, serving as the gating pulse for the analog signal that propagates by reflection between the two plates, applied across the top plate, directed towards the bottom plate and strongly focused on the crystalline medium beneath the area from where the analog signal is reflected, (iii) a preferably Avalanche Photo-Diode array placed immediately underneath the interference filter where the sum energy signals are collected.

20. A method for sampling an ultrafast optical analog signal that consists in (i) duplicating the ultrafast analog signal to be sampled into (n) copies, by splitting it to (n) equal branches, delaying each of the (n)th branches by (nT) and recombining all the branches, and (ii) feeding the (n) duplicated signal as in (i) to a non-linear, optical analog AND time-gate (iii) duplicating a shaped sampling pulse of temporal width ($\tau$) into (n) copies, by splitting it to (n) equal branches, delaying each (n)th branch by (nT+n$\tau$) femtoseconds and recombining all branches (iii) feeding the (n) duplicated sampling pulse of width ($\tau$) into the sampling gate of a non-linear, optical analog AND time-gate, so that each (n)th copy of the sampling pulse overlaps a temporal section of width ($\tau$) of the analog signal to be sampled, at a temporal distance of (n$\tau$) from its leading edge, (iv) collecting the sample signal outputs sequentially separated by nT femtoseconds each, in a fast photodetector, such as an Avalanche Photo-Diode or fast photo-multiplier.

21. The apparatus as in claim 20 wherein the optical analog AND time-gate is an SHG (second Harmonic Generation) crystal such as a KDP, KTP or BBO crystal, a photodetector having a band-gap larger than the energies of either the second or third light pulses but slightly smaller than the sum of the two such as an InGaAs or AlGaAs LED in respect to a 800 nm illuminating pulse of light, or a Raman amplifier consisting of a Raman-active medium such as Barium Nitrate Ba(NO$_3$)$_2$ or Calcium tungstate (CaWO$_4$), followed by a thresholding saturable absorber and a wavelength filter that transmits only the wavelength of the pulse of light emitted as a consequence of the interaction between the analog pulse and the sampling pulse and eliminates all light of different wavelengths.

* * * * *